United States Patent [19]

Muchowski et al.

[11] 4,001,295
[45] Jan. 4, 1977

[54] 11,12-DIFLUOROMETHYLENE SUBSTITUTED PROSTANOIC AND PROST-5-CIS-ENOIC ACID DERIVATIVES

[75] Inventors: Joseph M. Muchowski, Mexico City, Mexico; John H. Fried, Palo Alto, Calif.

[73] Assignee: Syntex (U.S.A.) Inc., Palo Alto, Calif.

[22] Filed: June 23, 1975

[21] Appl. No.: 589,219

[52] U.S. Cl. .................. 260/468 D; 260/239.1; 260/340.9; 260/343.3 R; 260/346.2 M; 260/501.16; 260/501.17; 260/514 D; 424/305; 424/317

[51] Int. Cl.[2] ....................................... C07C 177/00

[58] Field of Search ................... 260/468 D, 514 D

[56] References Cited

UNITED STATES PATENTS 3,725,454  4/1973  Beal ................................. 260/488
3,867,423  2/1975  Crabbe ............................. 260/468

Primary Examiner—Robert Gerstl
Attorney, Agent, or Firm—Gerard A. Blaufarb; William B. Walker

[57] ABSTRACT

Novel racemic and antimeric prostaglandin analogs having a difluoromethylene group attached to the C-11,12 positions of the molecule, and oxygenated functions at C-9 and C-15, which may be further substituted at C-15 by a methyl group and processes for the production of such compounds. Also included are the lower alkyl esters of the carboxylic acid function and pharmaceutically acceptable salts thereof. These compounds possess prostaglandin-like activities and thus are useful in the treatment of mammals, where prostaglandins are indicated.

38 Claims, No Drawings

11,12-DIFLUOROMETHYLENE SUBSTITUTED PROSTANOIC AND PROST-5-CIS-ENOIC ACID DERIVATIVES

The present invention relates to certain novel prostaglandin derivatives and to processes for the production thereof.

More particularly, the present invention relates to racemic and antimeric prostanoic and prost-5-cisenoic acid derivatives having a difluoromethylene (difluorocyclopropyl) group attached to the C-11,12 positions, and oxygenated functions at C-9 and C-15 positions of the molecule, which may be further substituted at C-15 by a methyl group, and to processes for the production of such compounds. Also included are the lower alkyl esters of the carboxylic acid function and pharmaceutically acceptable salts thereof.

Prostaglandins have classically been described as chemically related 20-carbon chain hydroxy fatty acids having the basic skeleton of prostanoic acid:

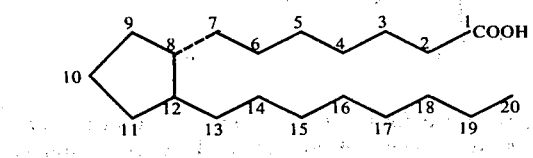

The prostaglandins having a keto group at the C-9 position are known as the PGE series, those having a hydroxyl group in place of the keto group are known as the PGF series and are further designated by an α or β suffix to indicate the configuration of the hydroxyl group at said position. The natural compounds are the 9α-hydroxy substituted compounds. They may contain different degrees of unsaturation in the molecule, particularly at C-5, C-13 and C-17, the unsaturation is also indicated by a suffix. For a review on prostaglandins and the difinition of primary prostaglandins, see for example S. Bergström, *Rescent Progress in Hormone Research* 22, pp. 153-175 (1966) and *Science* 157, page 382 (1967) by the same author.

Because of the remarkable range of biological and pharmacological properties exhibited by this family of compounds a great deal of interest has focused upon such compounds and the preparation of analogs of such compounds; accordingly, we have discovered processes and intermediates for preparing certain modified prostaglandins and derivatives thereof.

The novel prostaglandin derivatives of the present invention can be represented by the following generic formulas:

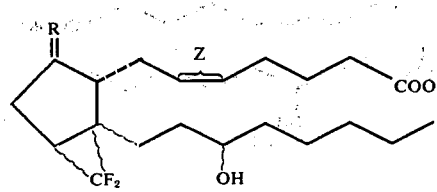

(A)

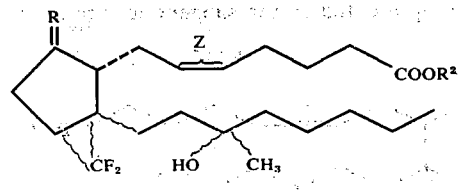

(B)

which comprises racemic mixtures and antimeric compounds,
wherein R is a keto group or α-hydroxy-β-hydrogen; $R^2$ is hydrogen, a lower alkyl group or the non-toxic, pharmaceutically acceptable salts of compounds in which $R^2$ is hydrogen;

Z represents a saturated linkage or a cis double bond; and the wavy lines ($\{$) indicate the α or β configuration or mixtures thereof, provided that when the side chain attached at the C-12 position is β, the difluoromethylene group at the C-11,12 positions is 11α,12α only and when the side chain attached at the C-12 position is α, the difluoromethylene group at the C-11,12 position is 11β,12β only.

The compounds of formula (A) above can be represented in further detail as follows:

The compounds wherein R is keto and the side chain attached at the C-12 position is β can be represented by the subgeneric formulas:

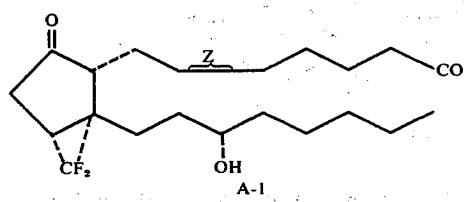
A-1

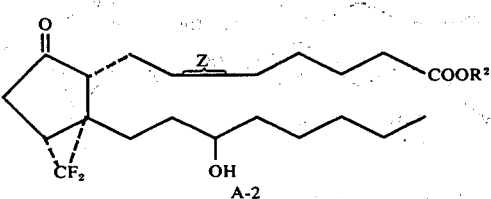
A-2

The compounds wherein R is α-hydroxy-β-hydrogen and the side chain attached at the C-12 position is β can be represented by the subgeneric formulas:

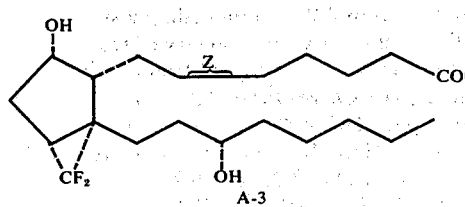
A-3

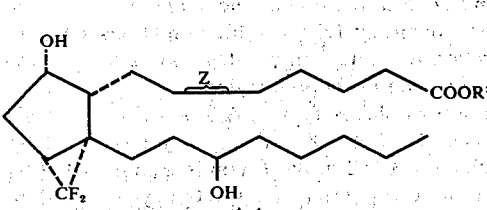
A-4

The compounds wherein R is keto and the side chain attached to the C-12 position is α can be represented by the subgeneric formulas:

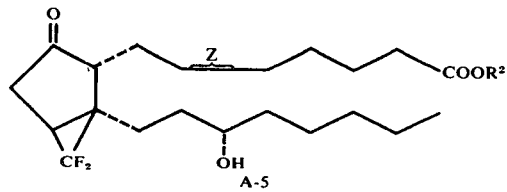
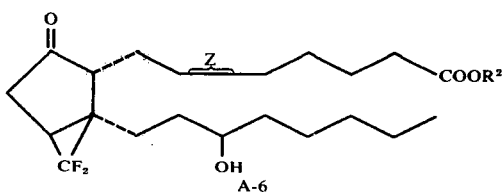

The compounds wherein R is α-hydroxy-β-hydrogen and the side chain attached to the C-12 position is α can be represented by the subgeneric formulas:

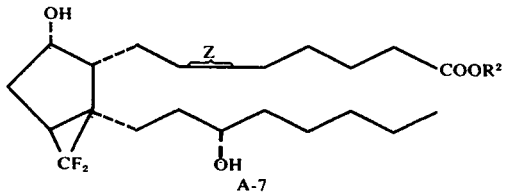
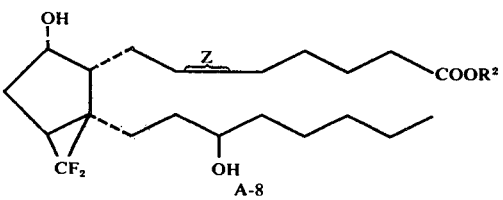

The compounds of formula (B) above in which the side chain attached to the C-12 position is β can be represented by the following subgeneric formulas:

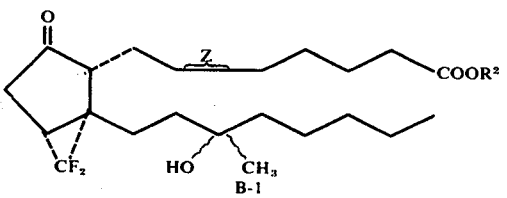
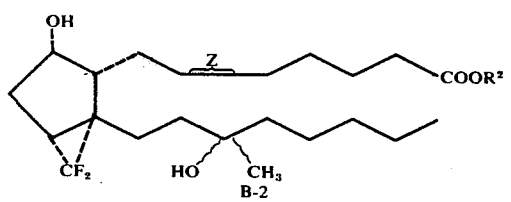

while the compounds of formula (B) in which the side chain attached to the C-12 position is α can be represented by the following subgeneric formulas:

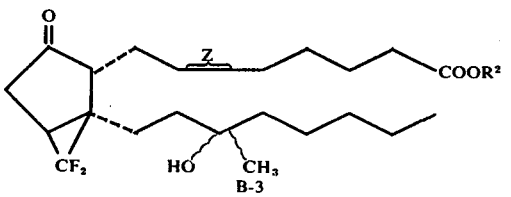
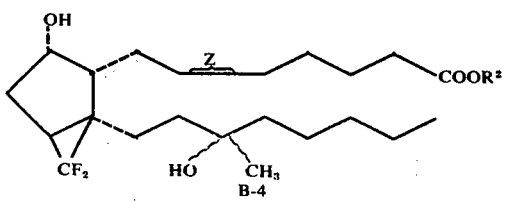

The dotted lines shown in the above formulas and in the formulas below indicate that the substituents are in α configuration, i.e., below the plane of the cyclopentane ring, solid line attachments indicate that the substituents are in β configuration, i.e., above the plane of the cyclopentane ring.

The unsaturation at C-5 in the prostenoic acid derivatives of the present invention (Z = double bond) has the same configuration as in natural prostaglandins of the E and F series, i.e., the cis configuration.

The compounds of formulas A-1, A-2, A-3, A-4, B-1 and B-2 have the side chain at C-8 in the α configuration and the side chain at C-12 in the β configuration, thus, the side chains are trans with respect to the cyclopentane nucleus, as in the natural prostaglandins, while the compounds of formulas A-5, A-6, A-7, A-8, B-3 and B-4 have the side chain at C-12 in the α-configuration, i.e., the side chains are (α,α) cis with respect to the cyclopentane nucleus.

These novel compounds possess several asymmetric centers and thus can exist in racemic (optically inactive) form as well as in either of the two enantiomeric, optically active forms. The racemic mixtures are encompassed by each of the above-depicted formulas (A-1 to B-4) and its mirror image.

For the sake of simplicity, only one antimer of each pair will be depicted in the following description and Claims; however, it is to be understood that the mirror images for the racemic mixtures and the individual antimers are encompassed thereby.

When the compounds of the present invention are racemic mixtures, they are produced starting from racemates, while the compounds of the invention are individual antimers the compounds are preferably obtained starting from the appropriate individual antimer.

The use of the symbol R or S preceding a substituent designates the absolute stereochemistry of that substituent according to the Cahn-Ingold-Prelog rules [see Cahn et al., Angew. Chem. Inter. Edit. Vol. 5, p. 385 (1966), errata p. 511; Cahn et al., Angew.Chem., Vol. 78, p. 413 (1966); Cahn & Ingold, J. Chem. Soc., (London), 1951, p. 612; Cahn et al., Experientia, Vol. 12, p. 81 (1956); Cahn, J. Chem. Educ., Vol. 41, p. 116 (1964)]. Because of the interrelation of the designated substituent with the other substituents in the compound having α or β prefixes, the designation of the absolute configuration of one substituent fixes the absolute configuration of all substituents in the compound and thus the absolute configuration of the compound as a whole.

The antimeric compounds of formulas A-1, A-2, A-5, A-6, B-1 and B-3 above are designated as 8R-antimers, while antimeric compounds of formulas A-3, A-4, A-7, A-8, B-2 and B-4 are designated as 8S-antimers.

The numbering system and the stereochemistry nomenclature used herein for the compounds of the present invention is the art accepted numbering and stereochemistry nomenclature [see *Progress in the Chemistry of Fats and Other Lipids*, Vol. IX, Part 2, pages 233–236 (1968) Pergamon Press, New York, and *J. Lipids Research*, Vol. 10, pages 316 to 319 (1969)]. The configuration for the alkyl side chain at C-12 is indicated only in the cases wherein said chain is attached in α-configuration to the cyclopentane ring, i.e., in opposite configuration to the configuration of natural prostaglandins.

The term "lower alkyl" as used herein refers to straight or branched alkyl groups containing from 1 to 4 carbon atoms inclusive, e.g., methyl, ethyl, n-propyl, isopropyl, n-butyl, t-butyl and the like. The preferred lower alkyl group is methyl.

The term "pharmaceutically acceptable salts" refers to salts prepared from pharmaceutically acceptable non-toxic bases, including inorganic basess and organic bases. Salts derived from inorganic bases include sodium, potassium, lithium, ammonia, calcium, magnesium, ferrous, zinc, copper, manganous, aluminum, ferric, manganic salts and the like. Particularly preferred are the ammonia, potassium, sodium, calcium and magnesium salts. Salts derived from pharmaceutically acceptable organic non-toxic bases include salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, chlorine and caffeine.

The novel compounds of the present invention can be obtained by several methods, as described hereinafter in detail.

Thus, the compounds of formula (A) in which Z is a saturated linkage can be prepared by catalytic hydrogenation of the corresponding Δ⁵-prostenoic or Δ⁵,¹³-prostadienoic acids or derivatives thereof as illustrated by the following overall sequence of reactions:

Sequence A

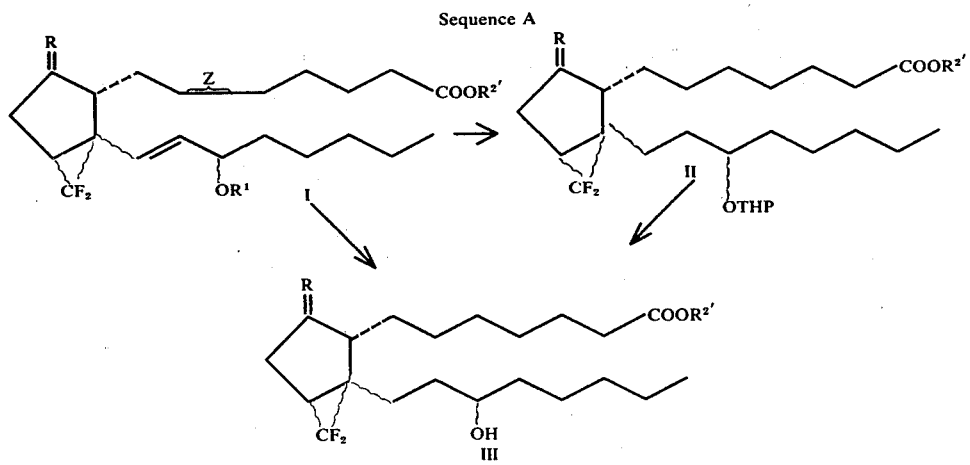

wherein
R, Z and the wavy lines ( ) are as defined above;
R²' is hydrogen or lower alkyl, particularly methyl;
R¹ is hydrogen or tetrahydropyranyl and
THP is tetrahydropyranyl.

In practicing the process outlined above, a racemic or antimeric compound of formula I is submitted to catalytic hydrogenation, in the presence of a palladium or platinum hydrogenation catalyst, using preferably 5% or 10% palladium-charcoal as catalyst, in an inert organic solvent, at a temperature comprised between about 0° to about 40° C, preferably at room temperature (about 25° C) and at atmospheric pressure or under slight pressure. The hydrogenation is allowed to proceed until one mole of hydrogen is consumed, in the case of using a monounsaturated compound (I, Z = saturated linkage) as starting material, or two moles of hydrogen when starting from prostadienoic acids (I, Z = double bond), to produce the saturated compounds of formulas II or III, depending upon the starting material used. When the hydrogenation is complete, the catalyst is separated by filtration and the product isolated from the filtrate by conventional means, i.e., evaporation of the solvent, preferably under reduced pressure, followed by purification of the residue by chromatography. Typically, there is used about 5 to 20% by weight of the catalyst, however, this is not critical, as good results are also obtained when using smaller or larger proportions. Suitable inert organic solvents for this reaction are methanol, ethyl acetate, tetrahydrofuran, dioxane and the like. The saturated compounds of formula II, obtained when using a 15-tetrahydropyranyloxy derivative as starting material (I, R¹ = tetrahydropyranyl), are submitted to a mild acid hydrolysis, e.g., treatment with aqueous acetic acid, using particularly 65% aqueous acetic acid, at room temperature or under slight heating, e.g., at about 40°

C for a period of time of the order of 6 to 24 hours, to afford also the compounds of formula III.
The 9α-hydroxy compounds of formula (A), both saturated and 5-cis unsaturated, can be obtained by the following process, in which, for the sake of clarity the four possible isomeric forms are depicted:
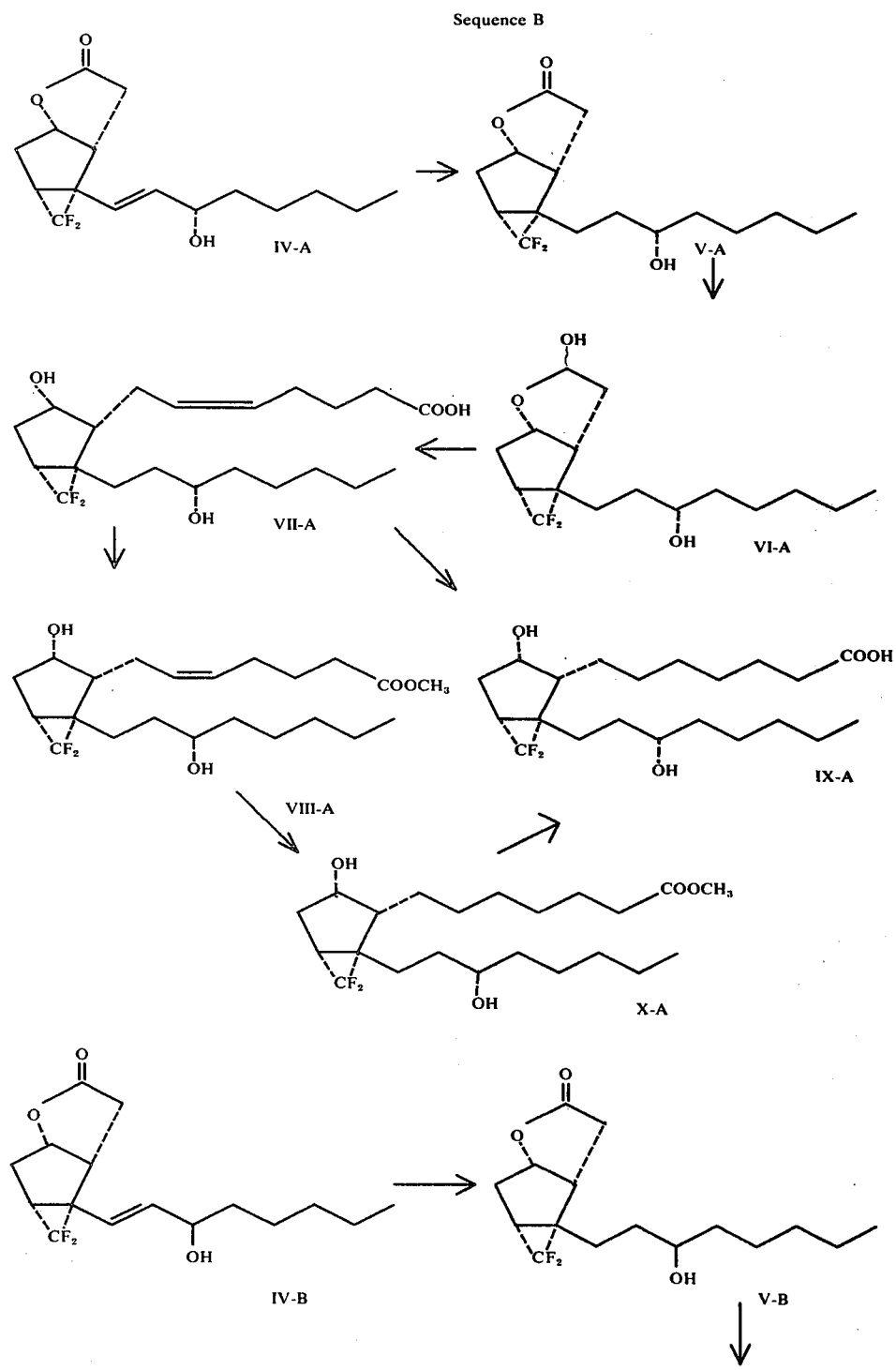
Sequence B -continued
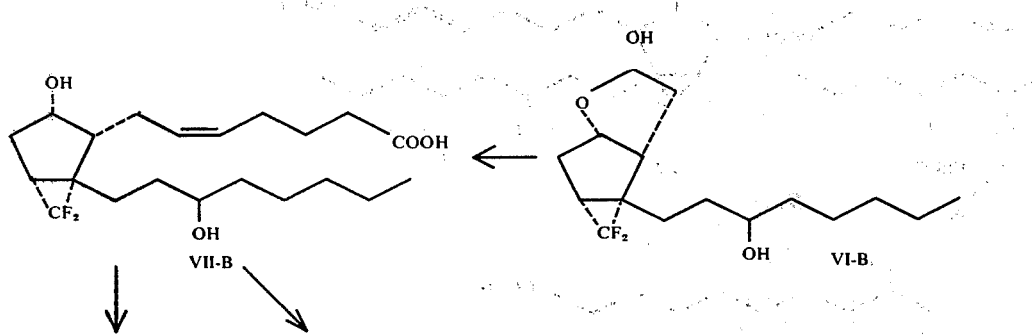
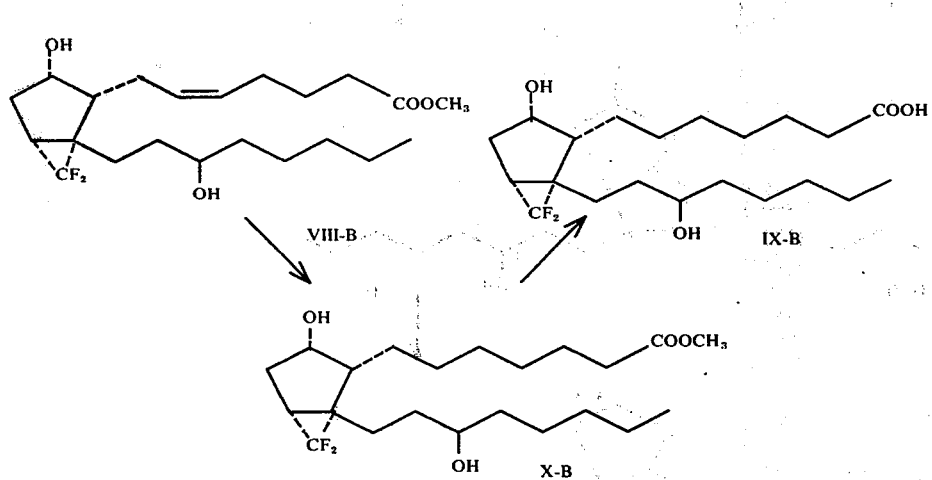
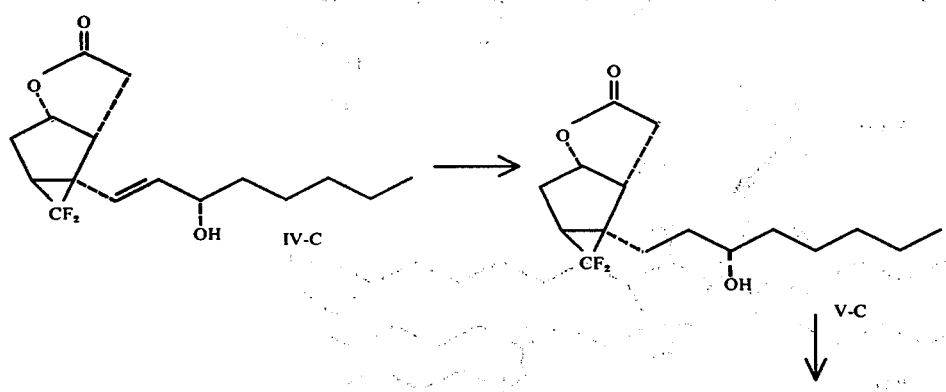
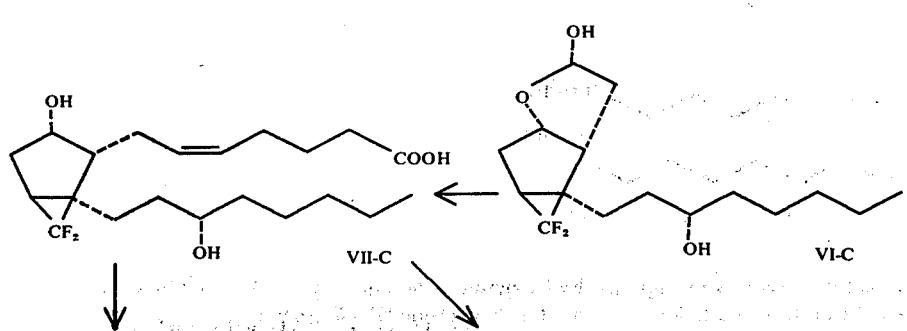

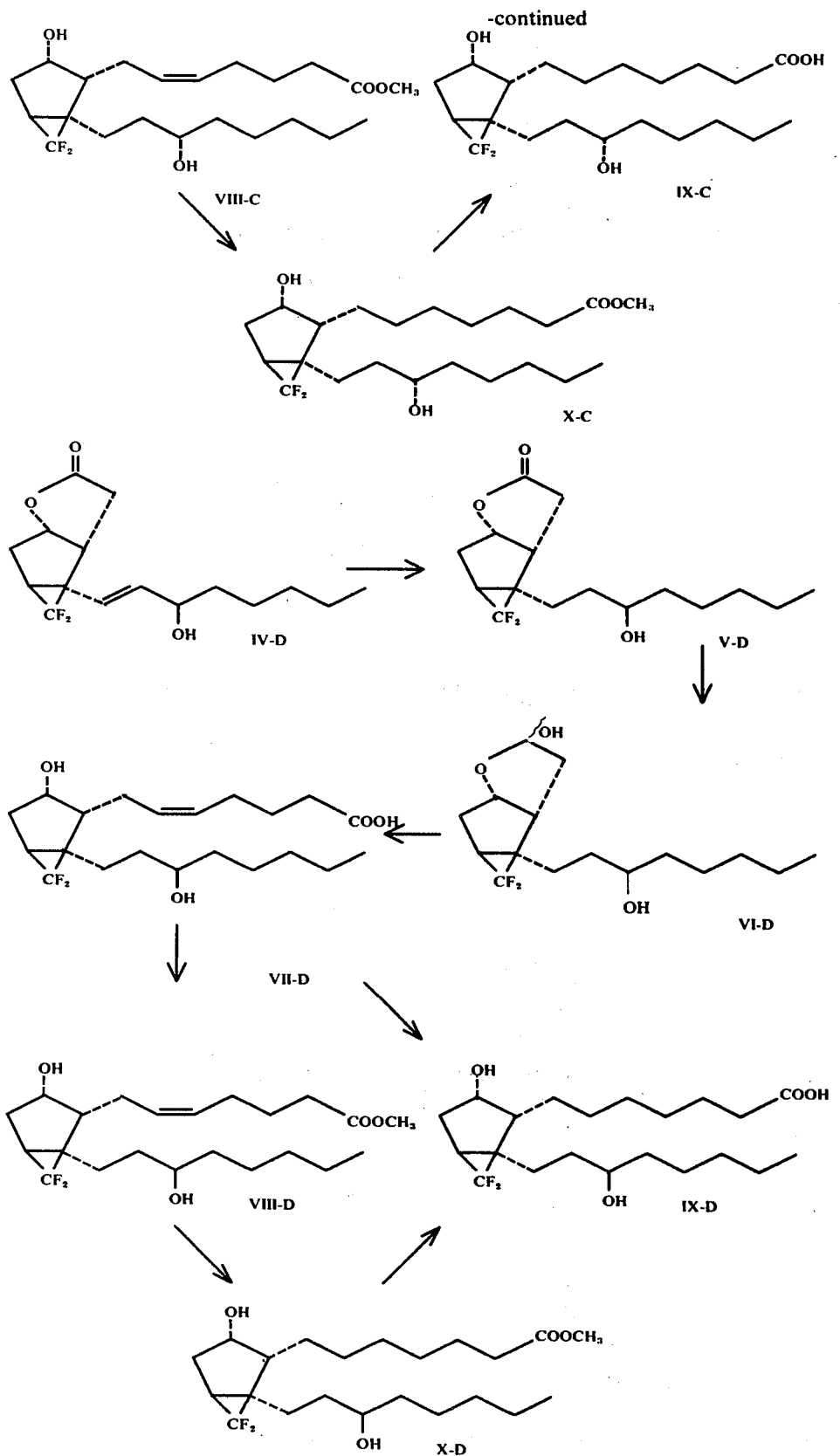

In practicing the process depicted above, when applied to the obtention of 11α,12α-difluoromethylene-15α-hydroxy compounds, the starting material, i.e., [2'α-hydroxy-4'α,5'α-difluoromethylene-5'β(3''α-hydroxyoct-1''(t)-en-1''-yl)cyclopent1'α-yl]acetic acid 1,2'-lactone (IV-A, racemic or 1'S-antimeric) is submitted to hydrogenation in the presence of Raney nickel as catalyst, in a suitable inert organic solvent, using particularly methanol as solvent, to produce the corresponding saturated compound of formula V-A.

The racemic or 1'S-antimeric lactol of formula VI-A can be prepared by reduction of the saturated lactone of formula V-A with about from 1.1 to 3 molar equivalents of diisobutylaluminum hydride in a suitable inert organic solvent. Typically, the reduction is conducted at about −70° C, for a short period of time, of the order of about 3 to about 10 minutes, using preferably about 1.8 to 2 molar equivalents of the diisobutylaluminum hydride. Suitable inert organic solvents for this reaction include, for example, the aromatic hydrocarbons such as toluene or xylene.

The racemic or 8S-antimeric prostenoic acid derivatives of formula VII-A can be prepared by condensation of the crude racemic or 1'S-antimeric lactol VI-A with the Wittig reagent derived from 5-triphenylphosphoniopentanoic acid and potassium dimethylsulfinyl carbanide, in dimethylsulfoxide solution.

This reaction is conducted under anhydrous conditions for about two to about 24 hours, at temperatures in the range of about from 15° to 50° C, preferably at about room temperature. This condensation is preferably carried out under an inert atmosphere, e.g., under argon or nitrogen atmosphere. Typically, the triphenylphosphoniopentanoic acid is used in an amount varying from about two to about five moles per mol of starting lactol VI-A and the amount of potassium dimethylsulfinyl carbanide varies between about two to about 10 moles. In the preferred embodiments 2.5 molar equivalents of the acid reagent and five molar equivalents of the carbanide reagent are used per mol of lactol. The product is obtained as the potassium salt, soluble in water, which can be converted to the free acid by acidification with oxalic acid, or other weak acid, to pH~5, followed by conventional extraction and evaporation. Preferably the prostaglandin derivative (VII-A) is further purified by thin-layer chromatography.

The 5-triphenylphosphoniopentanoic acid can be prepared according to the procedure described by R. Greenwald et al., in *J. Org. Chem.*, 28, 1128 (1963), from 5-bromopentanoic acid and triphenylphosphine in acetonitrile. The potassium dimethylsulfinyl carbanide can be obtained from potassium hydride and dimethylsulfoxide, stirring the mixture at room temperature until the evolution of gas ceases. Generally, it is preferred to prepare these reagents just prior to the reaction with the lactol of formula VI-A.

Alternatively, there can be used sodium dimethylsulfinyl carbanide.

Conventional esterification of the racemic or 8S-antimeric compound of formula VII-A with ethereal diazomethane gives rise to the methyl ester (VIII-A) which upon hydrogenation in the presence of a palladium catalyst, using preferably 5% palladium-charcoal as catalyst in a suitable inert organic solvent, e.g., methanol, ethanol, ethyl acetate and the like, using particularly ethyl acetate as solvent, produces the saturated racemic or 8S-antimeric methyl ester compound of formula X-A. This catalytic hydrogenation can also be carried out using the free acid of formula VII-A (racemic or 8S-antimeric) as starting material, to produce the racemic or 8S-antimeric compound of formula IX-A.

The free acid (IX-A) can be alternatively obtained by conventional saponification of the methyl ester (X-A) with base, i.e., by treatment with an alkali metal hydroxide or alkali metal carbonate in an aqueous lower aliphatic alcohol.

When the above-described process (IV-A through X-A) is performed using the isomeric compound having the hydroxy group in the β-configuration as starting material (IV-B) there will be obtained in each and every step of the process the corresponding racemic or 8S-antimeric 15β-substituted (prostaglandin numbering) derivative (V-B through X-B).

Similarly, when starting from the racemic or 1'S-antimeric compounds having the difluoromethylene group in the β-orientation and the hydroxyl group in the α-orientation (IV-C) there will be produced in each and every step of the process the corresponding racemic or antimeric compounds (V-C through X-C). Also, starting from compound of formula IV-D, there will be produced in each and every step of the process the corresponding racemic or antimeric compounds (V-D through X-D).

The racemic and 8R-antimeric 9-keto-5-unsaturated compounds of formula (A) can be prepared by the following reaction sequences:

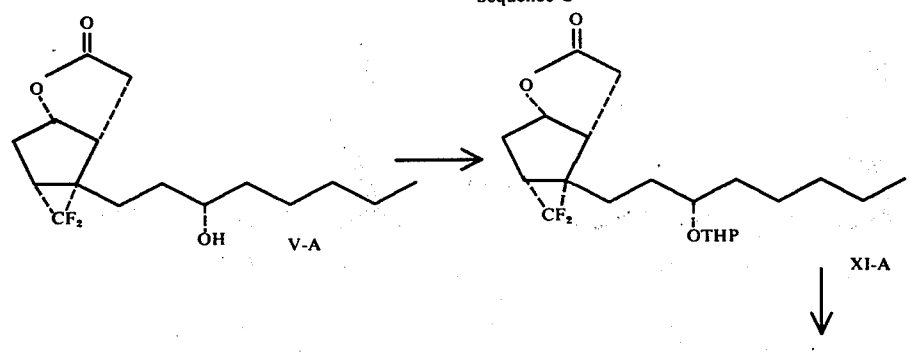

-continued
Sequence C
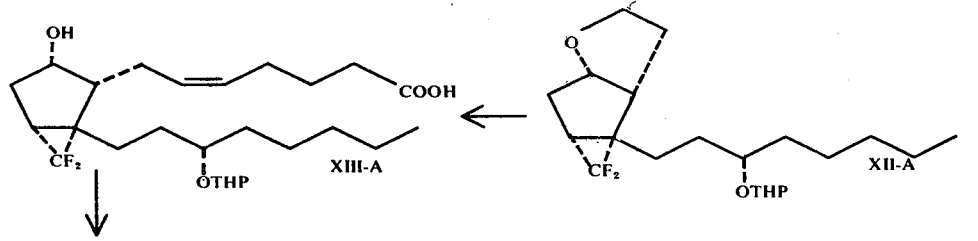
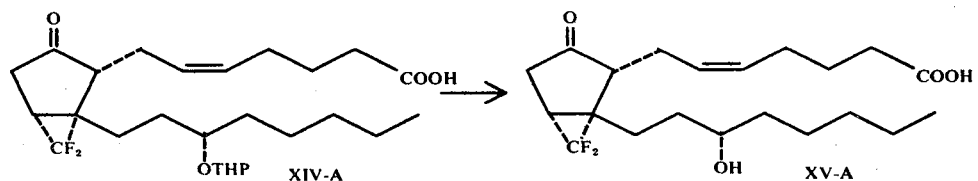
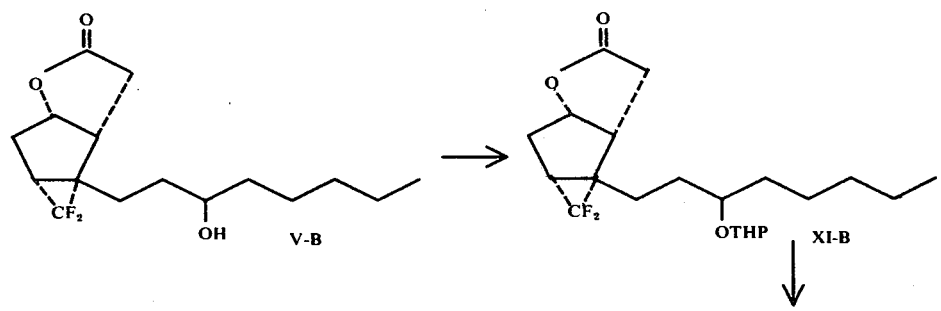
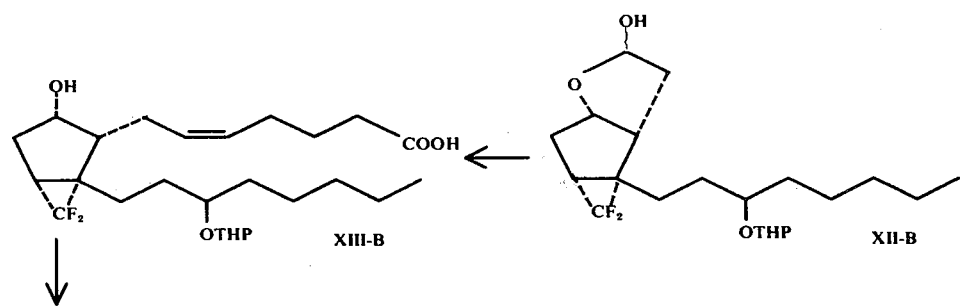
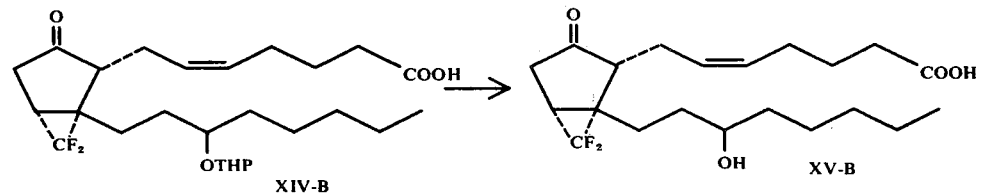
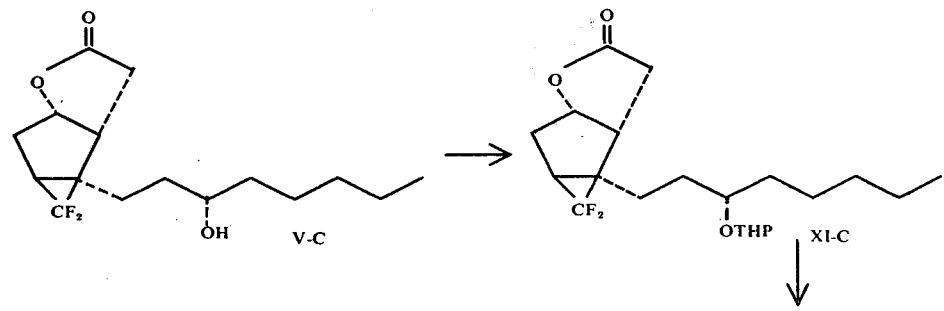

-continued
Sequence C

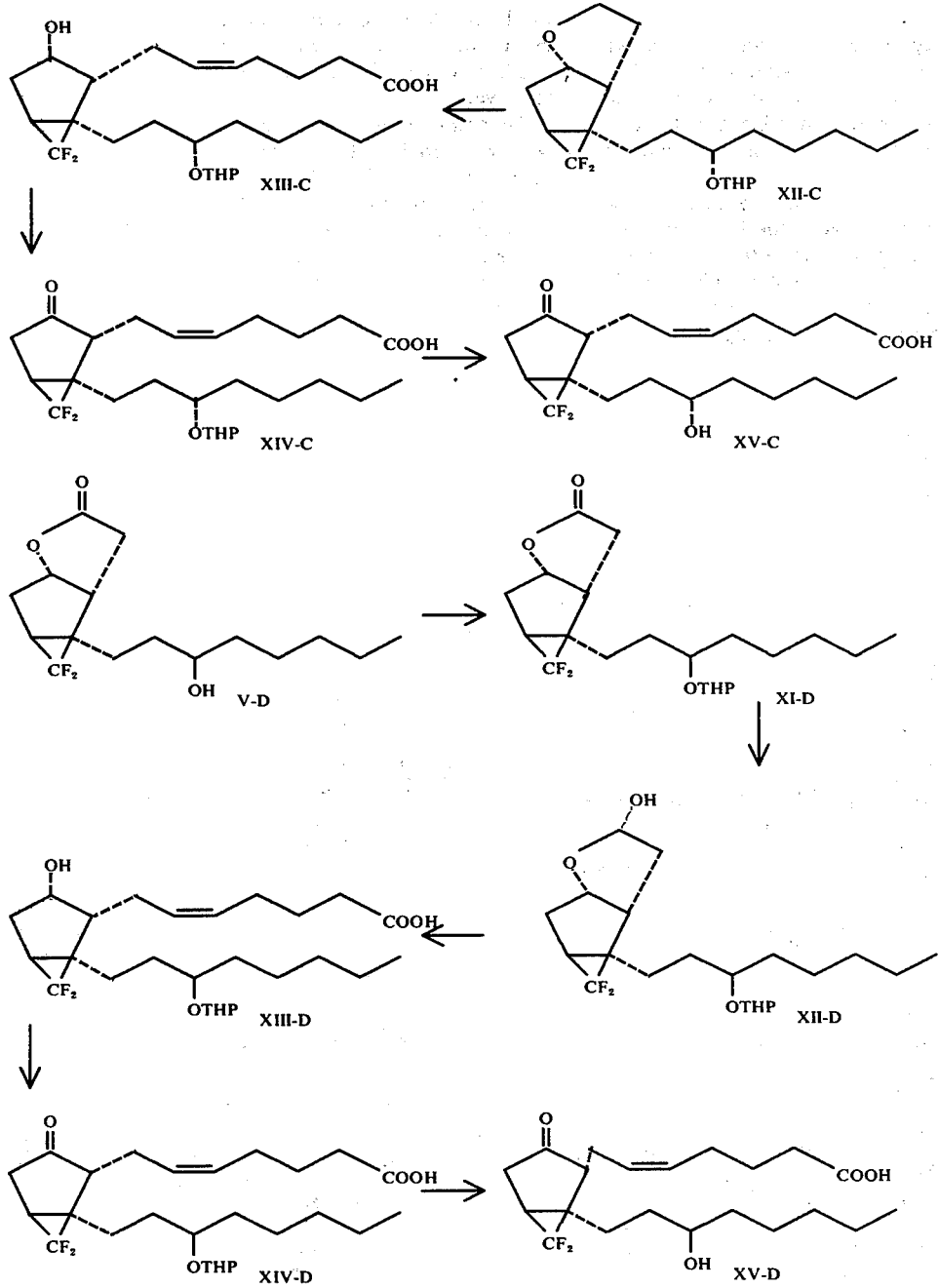

For the sake of clarity, the four possible isomeric forms are depicted.

With reference to the above sequence when applied to the obtention of 11α,12α-difluoromethylene-15α-hydroxy compounds the saturated lactone of formula V-A, (racemic or antimeric) prepared as described in sequence B, is etherified with dihydropyran in methylene chloride solution, in the presence of catalytic amounts of an acid catalyst, e.g., p-toluenesulfonic acid, under anhydrous conditions, to produce the tetrahydropyranyloxy derivative of formula XI-A. Typically, the reaction is conducted at room temperature for a short period of time, of the order of 5 to 30 minutes, using preferably about 2.5 molar equivalents of the reagent. The compound thus obtained is reduced to the lactol (XII-A), which in turn is condensed with the Wittig reagent derived from 5-triphenylphosphoniopentanoic acid and potassium dimethylsulfinyl carbanide, as described hereinbefore in detail with regard to Sequence B (V-A⟶VI-A⟶VII-A), to produce the racemic or 8S-antimeric-5-cisprostenoic acid compound of formula XIII-A.

Upon oxidation of compound XIII-A with chromic acid, using particularly an 8N chromic acid solution in acetone and sulfuric acid medium (Jones' reagent) there is produced the racemic or 8R-antimeric compound of formula XIV-A. This reaction is effected at low temperature, i.e., at about −20° to 0° C, for a period of time of about 30 minutes to 2 hours, using about 1.1 molar equivalents of the reagent per starting compound. Other chromic acid reagents are also practical e.g., chromium trioxide-diyridine trioxide-dipyridine (Collins' reagent).

The tetrahydropyranyloxy group is then hydrolyzed by mild acid treatment, i.e., by treatment with dilute acetic acid such as 65% aqueous acetic acid, at about room temperature or under slight heating, for about 18 to 50 hours, to produce the racemic or 8R-antimeric compound of formula XV-A.

When the above-described reaction sequence (V-A through XV-A) is carried out using the isomeric compound having the hydroxy group in the β-configuration as starting material (V-B) there will be obtained in each and every step of the process the corresponding 15β-substituted (prostaglandin numbering) derivative (XI-B through XV-B).

Similarly, when starting from racemic or antimeric compounds having the difluoromethylene group in the β-orientation and the hydroxy group in either the α or the β orientation (V-C) or (V-D), respectively, there will be produced in each and every step of the process the corresponding racemic or antimeric compounds (XI-C through XV-C) and (XI-D through XV-D), respectively.

The compounds of formula XV (A, B, C and D) can be converted into the corresponding saturated compounds by catalytic hydrogenation or into the methyl esters by treatment with diazomethane, as disclosed in Sequence B, as well as into other alkyl esters as described hereinafter in detail.

The racemic and antimeric compounds of formula (B) can be prepared by a process illustrated as follows:

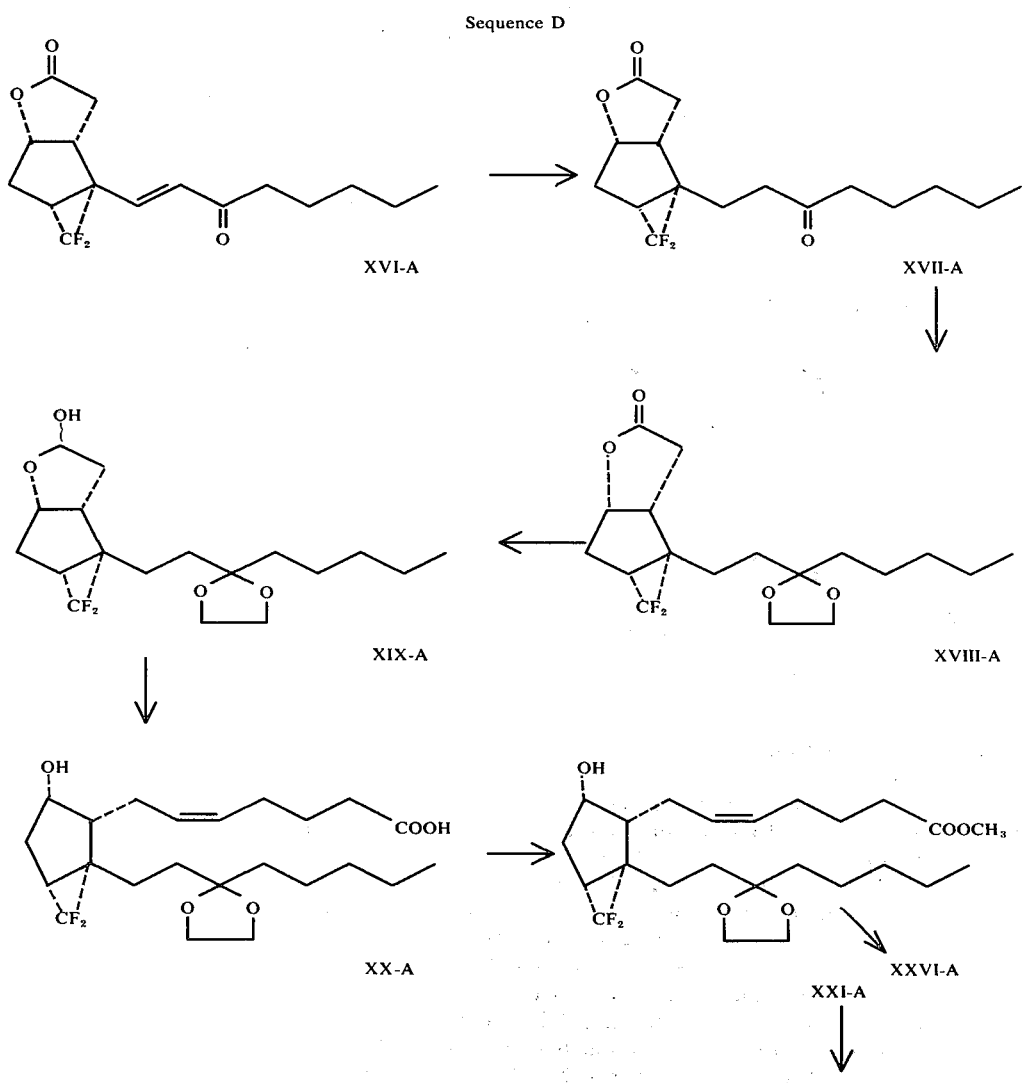

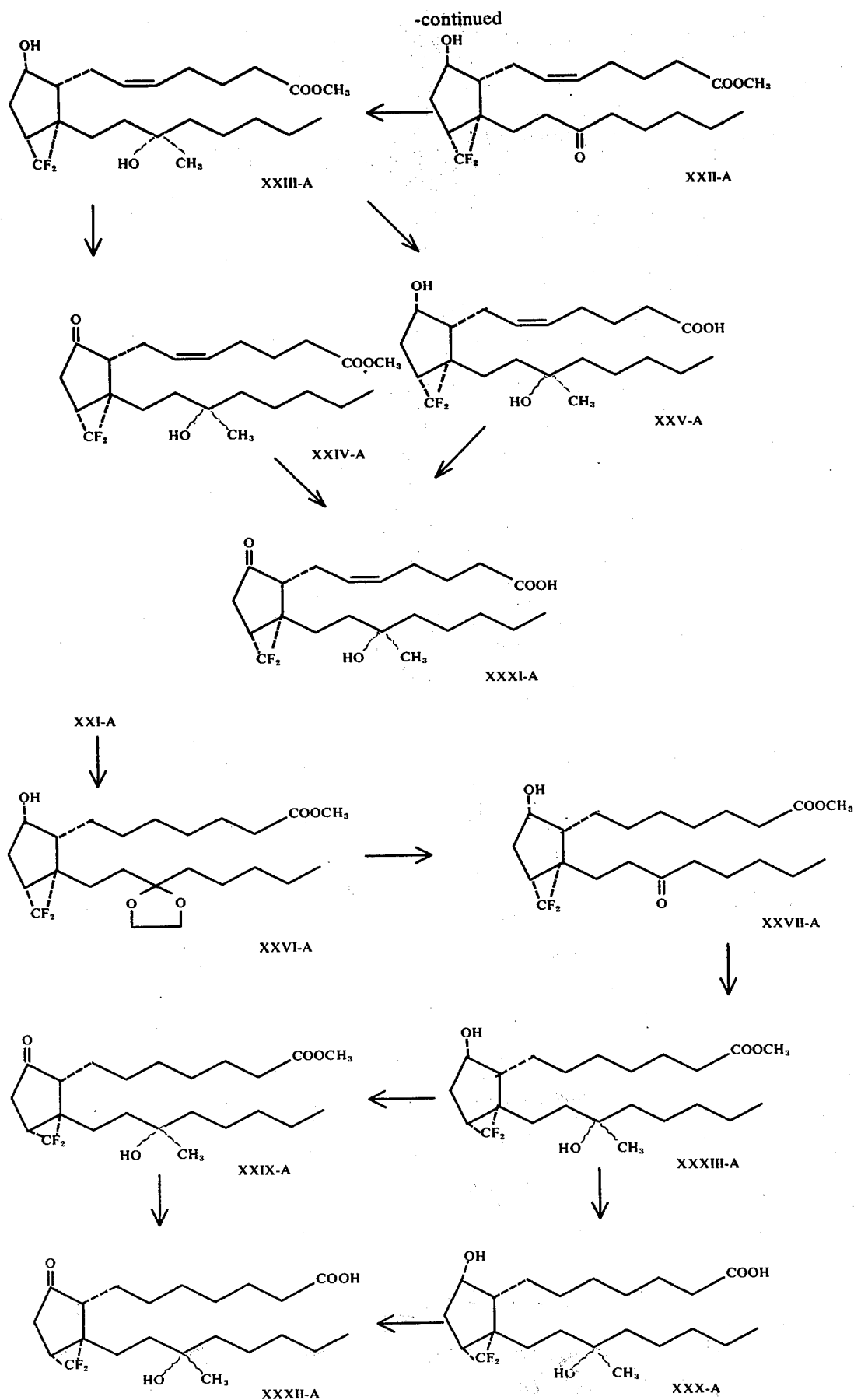

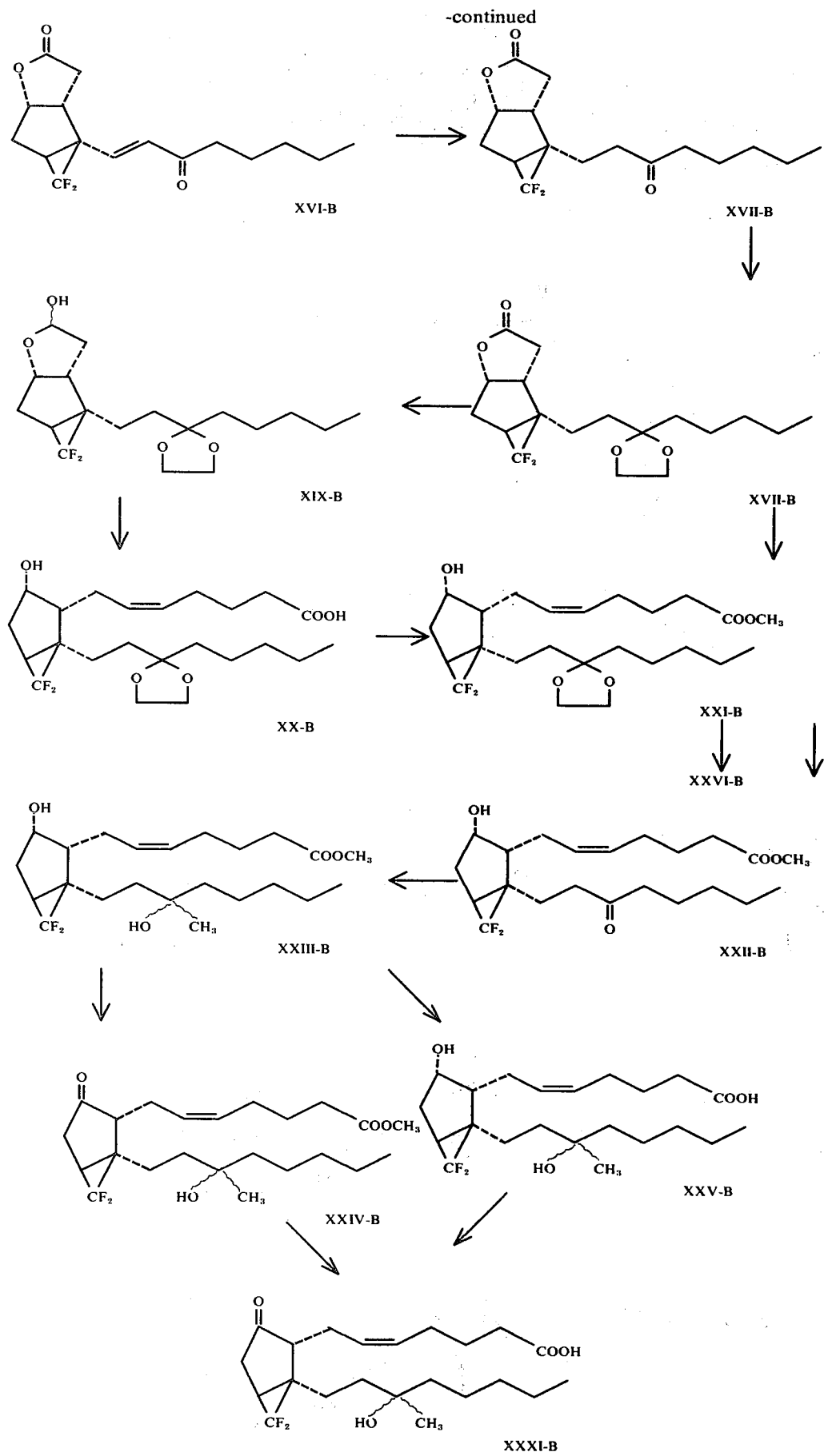

-continued

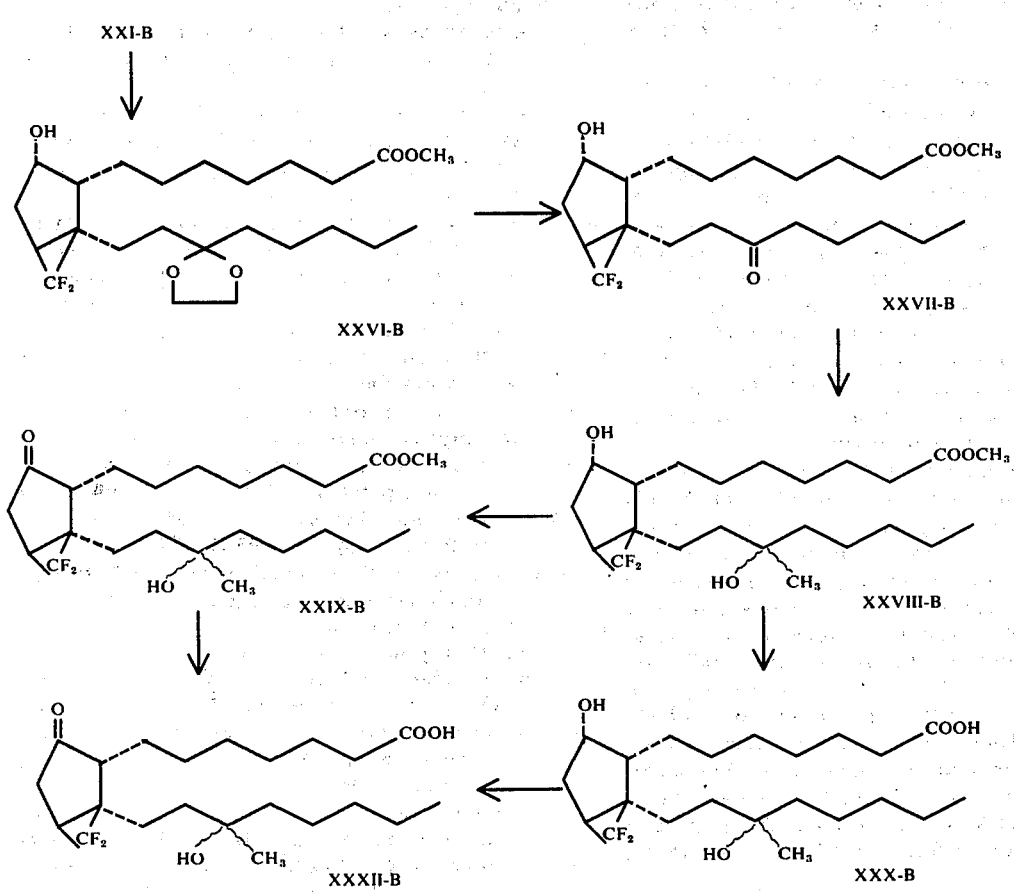

With reference to the above reaction sequence when applied to the 11α, 12α-difluoromethylene series the starting material, dl [2'α-hydroxy-4'α,5'α-difluoromethylene-5'β-(3''-oxo-oct-1'''(t)-en-1''-yl)cyclopent-1'α-yl]acetic acid 1,2'-lactone or its 1'S-antimer (XVI-A) is hydrogenated in the presence of Raney nickel, as previously described for Sequence B (IV-A→V-A), to produce the saturated compound of formula XVII-A. The oxo group in this keto-lactone is then protected as the ethylene ketal by treatment with ethyleneglycol in the presence of an acid catalyst, e.g., p-toluenesulfonic acid, in benzene solution for a prolonged period of time of the order of 18 to 24 hours to produce compound of formula XVIII-A, which is reduced to the lactol XIX-A, followed by condensation with 5-triphenylphosphoniopentanoic acid and potassium dimethylsulfinyl carbanide, as previously described in detail for sequence B (V-A →VI-A→VII-A) to produce the racemic or 8S-antimeric compound of formula XX-A.

Conventional esterification of the latter prostenoic acid derivative with ethereal diazomethane gives rise to the methyl ester (XXI-A). The ethylenedioxy protecting group is then cleaved by acid treatment, i.e., by treatment with an organic or inorganic acid such as perchloric acid, p-toluenesulfonic acid, acetic acid, hydrochloric acid and the like, in an aqueous suitable inert organic solvent, such as dimethoxyethane, acetone, tetrahydrofuran and the like, to produce the 15-keto compound of formula XXII-A. In the preferred embodiments, this reaction is carried out using catalytic amounts of 30% aqueous perchloric acid containing 5% of cupric sulfate, at about room temperature for a period of time of about 15 minutes to about 1 hour, preferably for about 30 minutes.

Upon reaction of the 15-keto compound (XXII-A) with a methylmagnesium halide there is obtained the 15 {-methyl- 15 } -hydroxy compound (racemic or 8S-antimeric) of formula XXIII-A, as a mixture of the 15α-methyl-15β-hydroxy-and 15β-methyl-15α-hydroxy epimers. This reaction is preferably carried out in ether or tetrahydrofuran solution, using from about 4 to about 10 molar equivalents of the Grignard reagent per molar equivalent of starting compound, at a temperature of between about −78°to about 0°C for a period of time of about 1 to about 6 hours, the reaction time depending upon the temperature at which the reaction takes place.

In the preferred embodiments, the reaction is conducted by adding the reagent portionwise to a previously cooled solution (−40° C) of compound (XxII-A) in tetrahydrofuran, under anhydrous conditions, stirring the resulting mixture at about −40°C and following the course of the reaction by thin layer chromatographic techniques. The reaction is usually complete within about 3 to about 4 hours.

Alternatively, the reaction can be carried out using methyllithium as reagent, however, a more selective alkylation is obtained when using a Grignard reagent, as described above.

Oxidation of the 9α-hydroxy group in the methylated racemic or 8S-antimeric compounds (XXIII-A) produces the corresponding 9-keto derivative of formula XXIV-A. This oxidation is preferably carried out using an excess of chromium trioxide-dipyridine complex as reagent in methylene chloride as solvent, conducting the reaction at about 0°C, for about 15 to about 30 minutes.

The methyl ester group in compound XXIII-A (racemic or antimeric) is eliminated by alkaline treatment, i.e., by treatment with an alkali metal hydroxide or alkali metal carbonate in an aqueous lower aliphatic alcohol, to produce the free acid of formula XXV-A. Typically this hydrolysis is effected using potassium carbonate as reagent and aqueous methanol as solvent, conducting the reaction at room temperature for a prolonged period of time, of the order of about 20 to about 60 hours. For the isolation of the product from the reaction mixture it is convenient to work it up under slightly acidic conditions, i.e., at a pH of about 6, by using a dilute solution of oxalic acid to avoid dehydration of the prostaglandin product.

Catalytic hydrogenation of the double bond in the racemic or 8S-antimeric compounds of formula XXI-A affords the corresponding saturated derivative of formula XXVI-A. The reaction conditions for this hydrogenation are the same as those previously described with regard to sequence B (VIII-A———►X-A), i.e., using preferably 5% palladium-charcoal as catalyst and ethyl acetate as solvent. The racemic or 8S-antimeric compound XXVI-A is then submitted to hydrolysis of the ethylenedioxy protecting group, alkylation of the 15-keto intermediate, and alkaline treatment, as described hereinbefore before in detail for the 5 monounsaturated compounds (XXI-A———►XXII-A —►XXIII-A—►XXV-A), to produce the respective saturated derivatives of formulas XXVII-A, XXVIII-A and XXX-A.

Upon oxidation of compound XXVIII-A (racemic 8S-antimeric) with chromium trioxide-dipyridine complex there is obtained the 9-keto-prostanoic acid methyl ester of formula XXIX-A (racemic or 8R-antimeric).

The 9-keto compounds of formulas XXIV-A and XXIX-A can be converted into the corresponding free acids (XXXI-A and XXXII-A, respectively) preferably by enzymatic hydrolysis methods, using for example, a recently extracted residue of the gorgonian Plexaura homomalla (Esper), in a saline solution, at a pH 7.5 to 7.7, as described by A. Prince et al., in *Prostaglandins*, Vol. 3, No. 4 p. 531 (1973), or by the action of other enzyme systems which are known as useful for the hydrolysis of compounds unstable to alkaline or acid conditions, such as a crude pancreatic lipase commercially available (Sigma Steapsin), a crude log pancreatic lipase, by the method described by A. F. Kluge et al., in J. Am. Chem. Soc. 94, 782 (1972) or baker's yeast [C. J. Sih et al., *J. C. S. Chem. Comm.* 240 (1972)].

Alternatively, the free acids of formulas XXXI-A and XXXII-A can be prepared by oxidation of the respective 9-hydroxy compounds of formulas XXV-A and XXX-A with chromium trioxide-dipyridine complex.

The hydrolysis of the methyl ester group in racemic or 8S-antimeric compounds of formulas XXIII-A and XXVIII-A to the respective free acids (XXV-A and XXX-A) can also be effected by the above-described enzymatic methods.

The compounds used as starting materials for sequences A, B and D, i.e., racemic and antimeric compounds of formula I, IV(A,B,C and D) and XVI (A and B) are known and can be prepared as described in U.S. Pat. No. 3,867,423.

The compounds of formula V (A, B, C and D) used as starting materials for sequence C, are intermediates in sequence B.

The alkyl ester derivatives of the prostanoic and prostenoic acid compounds of the present invention other than the methyl ester can be prepared by conventional treatment of the free acid with an excess of diazoalkane, i.e., diazoethane or diazopropane in ether or methylene chloride solution, in a conventional manner, or by reaction with the desired lower alkyl iodide in the presence of lithium carbonate, at room temperature.

The salt derivatives of the prostanoic and prostenoic acids of the present invention can be prepared by treating the corresponding free acids with about one molar equivalent of a pharmaceutically acceptable base, including inorganic and organic bases, per molar equivalent of free acid. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

The reaction is conducted in water, alone or in combination with an inert, water-miscible organic solvent, at a temperature of from about 0° to about 100° C, preferably at room temperature. Typical inert, water-miscible organic solvents include methanol, ethanol, isopropanol, butanol, acetone, dioxane or tetrahydrofuran. The molar ratio of the starting free acid to base used is chosen to provide the ratio desired for any particular salt. For preparing, for example, the calcium salts or magnesium salts, the free acid starting material can be treated with at least 0.5 molar equivalent of pharmaceutically acceptable base to yield a neutral salt. When the aluminum salts are prepared, at least one third molar equivalent of the pharmaceutically acceptable base is employed if a neutral salt product is desired.

In the preferred procedure, the calcium salts and magnesium salts can be prepared by treating the corresponding sodium or potassium salts with at least 0.5 molar equivalent of calcium chloride or magnesium chloride, respectively, in an aqueous solution, alone or in combination with an inert water-miscible organic solvent, at a temperature of from about 20° to about 100° C. Preferably, the aluminum salts of the prostanoic acids of the present invention can be prepared by treating the corresponding free acids with at least one third molar equivalent of an aluminum alkoxide, such as aluminum triethoxide, aluminum tripropoxide and the like, in a hydrocarbon solvent, such as benzene, xylene, cyclohexane, and the like at a temperature of from 20° to about 115° C. Similar procedures can be used to prepare salts of inorganic bases which are not sufficiently soluble for easy reaction.

The salt products are isolated by conventional means. For example, the reaction mixtures are evaporated to dryness, and the salts can be further purified by conventional methods.

The compounds of formulas (A) and (B) and/or salts exhibit prostaglandin-like biological activities and thus are useful in the treatment of mammals where the use of prostaglandins is indicated. They are bronchodilators and thus are useful in treating mammals for bronchial spasm or wherever strong bronchodilators are indicated. They are also useful in controlling or palliating hypertension in mammals and further exhibit central nervous system depressant activity in mammals, and are useful as sedatives. In addition, they are useful for inducing labor, in pregnancy, and for inducing menses to correct or reduce menstrual abnormalities.

The compounds of formulas (A) and (B) are particularly useful as bronchodilators, they control spasm and facilitate breathing, being thus indicated in conditions such as bronchial asthma, bronchitis, bronchiectasis, pneumonia and emphysema.

The compounds and/or salts of the invention can be administered in a wide variety of dosage forms, either alone or in combination with other pharmaceutically compatible medicaments, in the form of pharmaceutical compositions suited for oral or parenteral administration or inhalation in the case of bronchodilators. They are typically administered as pharmaceutical compositions consisting essentially of the free acids, esters or salts, of the invention, and a pharmaceutical carrier. The pharmaceutical carrier can be either a solid material, liquid or aerosol, in which the compound (free acid, ester or salt) is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups, or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, talcum, sodium bisulfite and the like.

For inhalation administration, the compounds i.e., free acids, esters or salts can, for example, be administered as an aerosol comprising the compounds or salts in an inert propellant together with a cosolvent (e.g., ethanol) together with optional preservatives and buffering agents. Additional general information concerning the inhalation administration of aerosols can be had by reference to U.S. Pat. Nos. 2,868,691 and 3,095,355.

The compounds of this invention are typically administered in dosages of about from 0.1 mg. to 100 mg. per Kg. of body weight. The precise effective dosage will, of course, vary depending upon de mode of administration, condition being treated and host.

The following examples illustrate the invention, but are not intended to limit its scope. When using racemic compounds as starting materials racemic compounds are obtained as products, while starting from antimeric compounds the products obtained are antimeric. The abbreviation t.l.c. refers to thin-layer chromatography; all mixture ratios used with regard to liquids refer to volume ratios, and the term room temperature designates a temperature of from 20° to 25° C. Also, where necessary, examples are repeated to provide sufficient starting materials for subsequent examples.

EXAMPLE 1

A. To a prehydrogenated suspension of 13 mg. of 5% palladium-charcoal catalyst in 5 ml. of ethyl acetate is added a solution of 125 mg. of dl 9-keto-11$\alpha$,12$\alpha$-difluoromethylene-15$\alpha$-tetrahydropyranyloxyprosta-5-cis,13-transdienoic acid in 5 ml. of ethyl acetate, and the resulting mixture is stirred under hydrogen atmosphere until no more hydrogen is absorbed (20 minutes), [t.l.c. analysis in methylene chloride-methanol (9:1) shows no remaining starting material]. The catalyst is then separated by filtration and washed with ethyl acetate. The combined filtrates are evaporated to dryness to give 118 mg. of dl 9-keto-11$\alpha$,12$\alpha$-difluoromethylene-15$\alpha$-tetrahydropyranyloxyprostanoic acid (racemic 11$\alpha$,12$\alpha$-difluoromethylene-15$\alpha$-isomeric form of II, R=keto, $R^{2'}$= hydrogen), as an oil, having an I.R. $\nu_{max}^{CHCL_3}$ 3400, 1740, 1705 cm$^{-1}$.

In another experiment methanol was substituted for ethyl acetate, obtaining the same results.

B. A mixture of 118 mg. of dl 9-keto-11$\alpha$, 12$\alpha$-difluoromethylene-15$\alpha$-tetrahydropyranyloxyprostanoic acid and 7 ml. of 65% aqueous acetic acid is stirred for 18 hours at room temperature. The solvent is then evaporated under reduced pressure and the residue purified by preparative thin layer chromatography using methylene chloride-methanol (90:10) as gradient, to produce 72 mg. of dl 9-keto- 11$\alpha$,12$\alpha$-difluoromethylene-15$\alpha$-hydroxyprostanoic acid (racemic 11$\alpha$,12$\alpha$-difluoromethylene-15$\alpha$-isomeric form of III, R = keto, $R^{2'}$= H,), an oil, which has the following constants:

| I.R. | $\nu_{max}^{CHCl_3}$ | 3420, 1745, 1710 cm$^{-1}$; |
|---|---|---|
| N.M.R. | $\delta_{TMS}^{CDCl_3}$ | 0.91 (t, 3H); 1.06–1.86 (m, 18H); 1.86–2.83 (m, 1H); 5.8 p.p.m. (m, 2H). |

By repeating the procedure described in part A of this Example but using dl 9-keto-11$\alpha$,12$\alpha$-difluoromethylene-15$\alpha$-hydroxyprosta-5-cis,13trans-dienoic acid and dl 9-keto-11$\alpha$,12$\alpha$-difluoromethylene-15$\alpha$-hydroxyprost-13-trans-enoic acid as starting materials in place of the tetrahydropyranylether derivatives there is also obtained in each case dl 9-keto-11$\alpha$,12$\alpha$-difluoromethylene-15$\alpha$-hydroxyprostanoic acid.

EXAMPLE 2

By following the methods of Example 1, parts A and B, dl 9$\alpha$-hydroxy-11$\alpha$,12$\alpha$-difluoromethylene-15$\alpha$-tetrahydropyranyloxyprosta-5-cis,13-trans-dienoic acid methyl ester and dl 9α-hydroxy-11β,12β-difluoromethylene-15α-tetrahydropyranyloxy-12α-prosta-5-cis,13-trans-dienoic acid are converted respectively into dl 11α,12α-difluoromethylene-9α,15α-dihydroxyprostanoic acid methyl ester and dl 11β,12β-difluoromethylene-9α,15α-dihydroxy-12α-prostanoic acid.

Likewise, by repeating the hydrogenation method of Example 1, 8R-9-keto-11α,12α-difluoromethylene-15α-hydroxyprosta-5-cis,13-trans-dienoic acid, 8S-11α,12α-difluoromethylene-9α,15α-dihydroxyprosta-5-cis,13-trans-dienoic acid and 8R-9-keto-11β,12β-difluoromethylene-15α-hydroxy-12α-prosta-5-cis,13-trans-dienoic acid are converted respectively into 8R-9-keto-11α,12α-difluoromethylene-15α-hydroxyprostanoic acid, 8S-11α,12α-difluoromethylene-9α,15α-dihydroxyprostanoic acid and 8R-9-keto-11β,12β-difluoromethylene-15α-hydroxy-12α-prostanoic acid.

EXAMPLE 3

A. A suspension of 200 mg. of Raney nickel [previously washed by decantation with water (2 × 5 ml.) and thereafter with 5 ml. of methanol]in 5 ml. of methanol is stirred under hydrogen atmosphere, at room temperature until no more hydrogen is taken up. A solution of 820 mg. of dl [2′α-hydroxy-4′α,5′α-difluoromethylene-5′β-(3″α-hydroxyoct-1″(t)-en-1‴-yl)cyclopent-1′α-yl]acetic acid 1,2′-lactone in 20 ml. of ethyl acetate is added and the resulting mixture is stirred under hydrogen. When no more hydrogen is absorbed, the catalyst is separated by filtration washing the solid with ethyl acetate. The combined filtrates are evaporated under vacuum, to produce 800 mg. of dl [2′α-hydroxy-4′α,5′α-difluoromethylene-5′β-(3″α-hydroxyoctan-1‴-yl)cyclopent-1′αyl]acetic acid 1,2′-lactone (racemic V-A), as an oil, which has the following constants:

4′α,5′α-difluoromethylene-5′β(3″β-hydroxyoctan-1‴-yl)cyclopent-1′α-yl]acetic acid 1,2′-lactone (racemic V-B) and dl [2′α-hydroxy-4′α,5′α-difluoromethylene-5′β(3″β-hydroxyoctan-1‴-yl)cyclopent-1″αyl]acetaldehyde 1,2′-hemiacetal (racemic VI-B).

Likewise, using dl [2′α-hydroxy-4′β,5′β-difluoromethylene-5′α(3″α-hydroxyoct-1″(t)-en-1‴-yl)cyclopent-1′α-yl]acetic acid 1,2′-lactone and dl [2′α-hydroxy-4′β,5′β-difluoromethylene-5′α(3″β-hydroxyoct-1‴(t)-en-1‴-yl)cyclopent-1′α-yl]acetic acid 1,2′-lactone as starting materials there are respectively produced as final products:

dl [2′α-hydroxy-4′β, 5′β-difluoromethylene-5′α(3′λ ′α-hydroxyoctan-1‴-yl)cyclopent-1′α-yl]acetaldehyde 1,2′-hemiacetal (racemic VI-C) and dl [2′α-hydroxy-4′β, 5′β-difluoromethylene-5′α(3′λ ′β- hydroxyoctan-1‴-yl)cyclopent-1′α-yl]acetaldehyde 1,2′-hemiacetal (racemic VI-D).

EXAMPLE 4

5-Triphenylphosphoniopentanoic acid (2.04 g) is dried for 2 hours (75° C/0.1 mm) and placed under an argon atmosphere. Dimethyl sulfoxide is added (3 ml.) to dissolve the solid and thereafter 4.39 ml. of 2M potassium dimethylsulfinylcarbanide in dimethylsulfoxide is added, with stirring, to yield a red solution. After 5 minutes, a solution of 565 mg. of crude dl [2′α-hydroxy-4′α,5′α-difluoromethylene-5′β-(3″α-hydroxyoctan-1β-yl)cyclopent-1′α-yl]acetaldehyde 1,2′-hemiacetal (1.85 mmol) in 4 ml. dimethyl sulfoxide is added.

The reaction mixture is stirred at room temperature for 20 hours, and then diluted with 25 ml. of cold water. The neutral components are removed by extraction with ethyl acetate-ether (1:1) (4 × 10ml). The aqueous phase is then acidified with oxalic acid to pH ~5 and extracted with 1:1 pentane-ether (5 × 10 ml.). The acidic extracts are washed with 5 ml. of saturated so-

| I.R. | | $\nu \, _{max}^{CHCl_3}$ | 3500, 1775 cm$^{-1}$; |
|---|---|---|---|
| N.M.R. | $\delta \, _{TMS}^{CDCl_3}$ | | 0.83 (t, 3H; 8″CH$_3$); 1.03–3.0 (m, 16H); 1.5–1.6 (m, 1H; OH; 3.1–3.70 (m, 1H; H-3″); 4.83–5.16 p.p.m. (m, 1H; H-2′). |

B. A solution of 800 mg. of dl [2′α-hydroxy-4′α,5′α-difluoromethylene-5′β-(3″α-hydroxyoctan-1‴-yl)cyclopent-1′α-yl]acetic acid 1,2′-lactone in 30 ml. of anhydrous toluene is cooled to −70° C, and to the cooled solution is added a 708 mg. portion of diisobutyl aluminum hydride in toluene. The course of the reaction is followed by thin-layer chromatographic analysis using hexane-ethyl acetate (30:70). After 5 minutes the reaction is complete, and then quenched by the dropwise addition of methanol until gas evolution ceases. The mixture is stirred for 15 minutes, diluted with 75 ml. of ethyl acetate and filtered through a pad of magnesium sulfate. Evaporation of the filtrate under vacuum affords 760 mg. of dl [2′α-hydroxy-4′α,5′α-difluoromethylene-5′β(3″α-hydroxyoctan-1‴-yl)cyclopent-1′α-yl]acetaldehyde 1,2′-hemiacetal (racemic VI-A), an oil, (I.R. $\theta_{max}^{CHCl_3}$ 3420 cm$^{-1}$).

In a similar manner starting from dl [2′α-hydroxy-4′α,5′α-difluoromethylene-5β(3″β-hydroxyoct-1″(t)-en-1‴-yl)cyclopent-1′α-yl]acetic acid 1,2′-lactone there are successively obtained dl [2′α-hydroxydium chloride solution, dried over anhydrous magnesium sulfate and evaporated to dryness under vacuum. The residue is purified by preparative thin layer chromatography using methylene chloride-methanol (9:1) as gradient, to produce 150 mg. of pure dl 11α,12α-difluoromethylene-9α,15α-dihydroxyprost-5-cis-enoic acid (racemic VII-A), an oil, which has the following constants:

| I.R. | | $\nu \, _{max}^{CHCl_3}$ | 3420, 1715 cm$^{-1}$; |
|---|---|---|---|
| N.M.R. | $\delta \, _{TMS}^{CDCl_3}$ | | 0.86 (t, 3H); 1.14–3.0 (m, 22H); 3.66–4.16 (m, 2H); 5.31–5.6 p.p.m. (m, 2H). |

By the same method dl [2′α-hydroxy-4′α,5′α-difluoromethylene-5′β-(3″βhydroxyoctan-1‴-yl)cyclopent- 1′α-yl]acetaldehyde 1,2′-hemiacetal is converted into dl 11α,12α-difluoromethylene-9α,15β-dihydroxyprost-5-cis-enoic acid (racemic VII-B), an oil, which has the following constants:

| | | | |
|---|---|---|---|
| I.R. | | $\nu \, ^{CHCl_3}_{max}$ 3420, 1715 cm$^{-1}$; | |
| N.M.R. | $\delta \, ^{CDCl_3}_{TMS}$ | 0.83 (t, 3H); 1.06—2.76 (m, 22H); 3.93–4.36 (m, 2H); 5.23–5.53 (m, 2H). | |

A solution of 260 mg. of dl 11α,12α-difluoromethylene-9α,15α-dihydroxyprost-5-cis-enoic acid in 10 ml. methylene chloride is treated with 15 ml. of an ethereal solution of diazomethane. After 5 minutes, no more starting material is present, as determined by t.l.c. analysis. The solvent is eliminated under vacuum and the residue purified by preparative t.l.c. using hexane-ethyl acetate (1:1) as eluant, to give 230 mg. of dl 11α,12α-difluoromethylene-9α,15α-dihydroxyprost-5-cis-enoic acid methyl ester (racemic VIII-A), an oil, having the following constants:

| I.R. | | $\nu \, ^{CHCl_3}_{max}$ 3500, 1730 cm$^{-1}$; |
|---|---|---|
| N.M.R. | $\delta \, ^{CDCL_3}_{TMS}$ | 0.87 (t, 3H); 1.17–2.6 (m, 22H); 1.54–1.8 (m, 2H); 3.63 (s, 3H); 4.15–4.4 (m, 2H); 5.33–5.52 p.p.m.(m, 2H); |
| M.S. (as di-trimethylsilyl ether) 475 (M$^+$—C$_5$H$_{11}$). | | |

Likewise, dl 11α,12α-difluoromethylene-9α, 15β-dihydroxyprost-5-cis-enoic acid is converted into dl 11α,12α-difluoromethylene-9α,15α-dihydroxyprost-5-cis-enoic acid methyl ester (racemic -hemiacetal an oil, which has the following constants:

| I.R. | | $\nu \, ^{CHCl_3}_{max}$ 3500, 1730 cm$^{-1}$; |
|---|---|---|
| N.M.R. | $\delta \, ^{CDCl_3}_{TMS}$ | 0.87 (t, 3H; 20-CH$_3$); 1.17–2.7 (m, 22H); 1.62–1.73 (m, 2H; OH's); 3.63 (s, 3H; COOCH$_3$); 4.13–4.4 (m, 2H; H-9, 15); 5.28–5.56 p.p.m. (m, 2H; H-5,6); |
| M.S. (as ditrimethylsilyl ether) 531 (M$^+$ —CH$_3$). | | |

By repeating the procedures of this Example using dl [2'α-hydroxy-4'β, 5'β-difluoromethylene-5'α-(3''α-hydroxyoctan-1''-yl)cyclopent-1'α-yl]acetaldehyde 1,2'-hemiacetal and dl [2,'α-hydroxy-4'β,5'β-difluoromethylene-5'α-(3''β-hydroxyoctan-1''-yl)cyclopent-1'α-yl]acetaldehyde 1,2'-hemiacetal as starting materials, there are respectively obtained dl 11β,12β-difluoromethylene-9α,15β-dihydroxy-12α-prost-5-cis-enoic acid (racemic VII-C) and dl 11β,12β-difluoromethylene- 9α,15β-dihydroxy-12α-prost-5-cis-enoic acid (racemic VII-D) as well as the corresponding methyl esters.

EXAMPLE 5

A suspension of 10 mg. of 5% palladium-charcoal catalyst in 4 ml. of ethyl acetate is stirred under hydrogen atmosphere, at room temperature, until no more hydrogen is absorbed. A solution of 70 mg. of dl 11α, 12α-difluoromethylene-9α,15α-dihydroxyprost-5-cis-enoic acid in 10 ml. of ethyl acetate is then added and the reaction mixture stirred under hydrogen atmosphere until no more hydrogen is absorbed. The catalyst is separated by filtration and the filtrate evaporated to dryness under vacuum, to afford 67 mg. of dl 11α,12α-difluoromethylene-9α,15α-dihydroxyprostanoic acid (racemic IX-A), an oil, having the following constants:

| I.R. | | $\nu \, ^{CHCl_3}_{max}$ 3400, 1715 cm$^{-1}$; |
|---|---|---|
| N.M.R. | $\delta \, ^{CDCl_3}_{TMS}$ | 0.9 (t, 3H); 1.06–2.66 (m, 26H); 3.33–3.7 (m, 1H); 4.0 (m, 3H); 4.0–4.5 p.p.m. (m, 1H). |

By the same method, starting from 230 mg. of dl 11α,12α-difluoromethylene-9α,15α-dihydroxyprost-5-cis-enoic acid methyl ester there are obtained 214 mg. of dl 11α,12α-difluoromethylene-9α,15α-dihydroxyprostanoic acid methyl ester (racemic X-A), an oil, having the following constants:

| I.R. | | $\nu \, ^{CHCl_3}_{max}$ 3500, 1730 cm$^{-1}$; |
|---|---|---|
| N.M.R. | $\delta \, ^{CDCl_3}_{TMS}$ | 0.88 (t, 3H); 1.17–2.7 (m, 26H); 1.92–2.22 (m, 2H); 3.64 (s, 3H); 4.1–4.4 p.p.m. (m, 2H); |
| M.S. (as ditrimethylsilyl ether) 528 (M$^+$—HE). | | |

In a similar manner starting from dl 11α,12α-difluoromethylene-9α,15α-dihydroxyprost-5-cis-enoic acid there is obtained dl 11α,12α-difluoromethylene-9α,15β-dihydroxyprostanoic acid (racemic IX-B), an oil, which has the following constants:

| I.R. | $\nu_{max}^{CHCl_3}$ | 3420, 1715 cm$^{-1}$; |
|---|---|---|
| N.M.R. | $\delta_{TMS}^{CDCl_3}$ | 0.89 (t, 3H); 1.03–2.65 (m, 26H); 3.4–3.7 (m, 2H); 3.8–4.1 p.p.m. (m, 3H). |

When using dl 11α,12α-difluoromethylene-9α,15β-dihydroxyprost-5-cis-enoic acid methyl ester as starting material in the procedure of this Example there is obtained dl 11α,12α-difluoromethylene-9α,15β-dihydroxyprostanoic acid methyl ester (racemic X-B), an oil, which has the following constants:

| I.R. | $\nu_{max}^{CHCl_3}$ | 3480, 1730 cm$^{-1}$; |
|---|---|---|
| N.M.R. | $\delta_{TMS}^{CDCl_3}$ | 0.88 (t, 3H); 1.17–2.7 (m, 26H); 1.61–1.90 (m, 2H); 3.63 (s, 3H); 4.13–4.38 p.p.m. (m, 2H); |
| M.S. (as ditrimethylsilyl ether) 477 (M$^+$ —CH$_3$). | | |

EXAMPLE 6

A. To a solution of 595 mg. of dl [2'α-hydroxy-4'α,5'α-difluoromethylene-5'β-(3''α-hydroxyoctan-1''-yl)cyclopent-1'α-yl]acetic acid 1,2'-lactone in 7 ml. of dry methylene chloride is added 4 mg. of p-toluenesulfonic acid and 0.4 ml. of freshly distilled 2,3-dihydropyran. The mixture is stirred at room temperature, and the course of the reaction is followed by t.l.c. [hexane-ethyl acetate (30:70)]. After 10 minutes, the reaction is complete. It is quenched by the addition of 5 drops of pyridine and then diluted with 50 ml. of methylene chloride. The solution thus obtained is washed with 10 ml. of saturated sodium chloride solution, dried over magnesium sulfate and evaporated to dryness under vacuum, to yield 620 mg. of dl [2'α-hydroxy-4'α,5'α-difluoromethylene-5'β-(3''α-tetrahydropyranyloxyoctan-1''-yl)cyclopent-1'α-yl]acetic acid 1,2'-lactone (racemic XI-A), an oil, having an I.R. $\theta_{max}^{CHCl_3}$ 1780 cm$^{-1}$. CHCl B. To a solution of 620 mg. of dl [2'α-hydroxy-4'α,5'α-difluoromethylene-5'β-(3''α-tetrahydropyranyloxyoctan-1''-yl)cyclopent-1'α-yl]acetic acid 1,2'-lactone in 30 ml. of anhydrous toluene previously cooled to −70° C is added dropwise a solution of 552 mg. of diisobutyl-aluminum hydride in 10 ml. of toluene. The reaction mixture is stirred at −70° C following the course of the reaction by t.l.c. [hexane-ethyl acetate (1:1)] until no more starting material is present (10 minutes). It is then quenched by the addition of a few drops of methanol, and stirred for an additional 15 minute period, diluted with 60 ml. of ethyl acetate and filtered through a pad of magnesium sulfate. The filtrate is evaporated under reduced pressure to give 585 mg. of dl [2'α-hydroxy-4'α,5'α-difluoromethylene-5'β-(3''α-tetrahydropyranyloxyoctan-1''-yl)cyclopent-1'α-yl]acetaldehyde 1,2'-hemiacetal (racemic XII-A), an oil having an I.R. $\theta_{max}^{CHCl_3}$ 3440 cm$^{-1}$.

C. 5-Triphenylphosphoniopentanoic acid (1.65 g.), is dried for 2 hours (75° C/0.1 mm) and is then placed under an argon atmosphere. Dimethyl sulfoxide (4 ml) is added to dissolve the solid and thereafter 3.56 ml. of 2M potassium methylsulfinyl carbanide in dimethyl sulfoxide, under stirring. To the red solution thus obtained is added, after 5 minutes, a solution of 585 mg. of dl [2'α-hydroxy-4'α,5'α-difluoromethylene-5'β-(3''α-tetrahydropyranyloxyoctan-1''yl)cyclopent-1'α-yl]acetaldehyde 1,2'-hemiacetal in 1.5 ml. of dimethyl sulfoxide. The reaction mixture is stirred for 1 hour, diluted with 20 ml. of ice-water and extracted with ethyl acetate-ether (1:1) (4 × 10 ml) to remove the neutral components. The aqueous phase is then acidified with oxalic acid to pH~5 and extracted with pentane-ether (1:1) (5 × 10 ml). The combined acidic extracts are washed with 5 ml. of sodium chloride solution, dried over magnesium sulfate and evaporated to dryness under reduced pressure. The residue is purified by preparative thin layer chromatography using methylene chloride-methanol (95:5) as eluant, to give 420 mg. of pure dl 11α,12α-difluoromethylene-9α-hydroxy-15α-tetrahydropyranyloxyprost-5-cis-enoic acid (racemic XIII-A), an oil, having an I.R. $\theta_{max}^{CHCl_3}$ 3500, 1710 cm$^{-1}$.

D. A cold solution (−10° C) of 420 mg. of dl 11α,12α-difluoromethylene-9α-hydroxy-15α-tetrahydropyranyloxyprost-5-cis-enoic acid in 10 ml. of purified acetone is treated dropwise over a 5 minute period, with 0.39 ml. of an 8N solution of chromic acid. The reaction mixture is stirred for 1 hour at the same temperature and then 0.39 ml. of isopropyl alcohol are added. The resulting mixture is stirred for 5 minutes and diluted with 30 ml. of ethyl acetate. The organic layer is washed with water (3 × 3 ml), and saturated sodium chloride solution (3 ml), dried over anhydrous magnesium sulfate and evaporated to dryness under vacuum to yield 395 mg. of dl 9-keto-11α,12α-difluoromethylene-15α-tetrahydropyranyloxyprost-5-cis-enoic acid (racemic XIV-A), an oil having an I.R. $\theta_{max}^{CHCl_3}$ 3500, 1740, 1715 cm$^{-1}$.

E. A mixture of 395 mg. of crude dl 9-keto-11α,12α-difluoromethylene-15α-tetrahydropyranyloxyprost-5-cis-enoic acid and 10 ml. of 65% acetic acid is stirred at room temperature for 40 hours. The solvent is then removed under reduced pressure, and the residue purified by thin layer chromatography using methylene chloride-methanol (90:10) as eluant to yield 280 mg. of pure dl 9-keto-11α,12α-difluoromethylene-15α-hydroxyprost-5-cis-enoic acid (racemic XV-A), an oil, which has the following constants:

| I.R. | $\nu_{max}^{CHCL_3}$ | 3420, 1750, 1715 cm$^{-1}$; |
|---|---|---|
| N.M.R. | $\delta_{TMS}^{CDCl_3}$ | 0.88 (t, 3H); 1.16–2.8 (m, 22H); 3.45–3.75 (m, 1H); 5.25–5.75 p.p.m. (m, 4H). |

EXAMPLE 7

Example 6 is repeated using as starting material dl [2'α-hydroxy-4'α,5'α-difluoromethylene-5'β-(3''β-hydroxyoctan-1''-yl)cyclopent-1'α-yl]acetic acid 1,2'-lactone, to produce successively:

dl [2'α-hydroxy-4'α,5'α-difluoromethylene-5'β-(3'λ'β-tetrahydropyranyloxyoctan-1''-yl)cyclopent-1'α-yl]acetic acid 1,2'-lactone, (racemic XI-B);

dl [2'α-hydroxy-4'α,5'α-difluoromethylene-5'β-(3'λ'β-tetrahydropyranyloxyoctan-1''-yl)cyclopent-1'α-yl]acetaldehyde 1,2'-hemiacetal (racemic XII-B);

dl 11α,12α-difluoromethylene-9α-hydroxy-15β-tetrahydropyranyloxyprost-5-cis-enoic acid (racemic XIII-B);

dl 9-keto-11α,12α-difluoromethylene-15β-tetrahydropyranyloxyprost-5-cis-enoic acid (racemic XIV-B) and dl 9-keto-11α,12α-difluoromethylene-15β-hydroxy-prost-5-cis-enoic acid (racemic XV-B), an oil, which has the following constants:

| I.R. | $\nu_{max}^{CHCl_3}$ | 3440, 1745, 1715 cm$^{-1}$; |
|---|---|---|
| N.M.R. | $\delta_{TMS}^{CDCl_3}$ | 0.88 (t, 3H); 1.1–2.9 (m, 22H); 3.46–3.73 (m, 1H); 4.23–4.56 (m, 2H); 5.34–5.6 p.p.m. (m, 2H). |

Likewise but using dl [2'α-hydroxy-4'β,5'β-difluoromethylene-5'β-(3''α-hydroxyoctan-1''-yl)cyclopent-1'α-yl] acetic acid 1,2'-lactone and dl [2'α-hydroxy-4'β,5'β-difluoromethylene-5'α-(3''β-hydroxyoctan-1''-yl)cyclopent-1'α-yl]acetic acid 1,2'-lactone there are produced as final products dl 9-keto-11β,12β-difluoromethylene-15α-hydroxy-12α-prost-5-cis-enoic acid (racemic XV-C) and dl 9-keto-11β,12β-difluoromethylene-15β-hydroxy-12α-prost-5-cis-enoic acid (racemic XV-D), respectively.

EXAMPLE 8

A. To a prehydrogenated suspension of 450 mg. of Raney nickel (previously washed twice with 5 ml. of water and then with 5 ml. of methanol) in 10 ml. of methanol is added a solution of 2.5 g. of dl [2'α-hydroxy-4'α,5'α-difluoromethylene-5'β-(3''-oxo-oct-1'''(t)-en-1''-yl)cyclopent-1''α-yl]acetic acid 1,2'-lactone in 50 ml. of ethyl acetate and the resulting mixture is stirred under hydrogen atmosphere until no more hydrogen is absorbed. The catalyst is separated by filtration and washed with ethyl acetate. The combined filtrates are evaporated to dryness under vacuum to yield dl [2'α-hydroxy-4'α,5'α-difluoromethylene-5'β(-3''-oxo-octan-1''-yl)cyclopent-1'α-yl]acetic acid 1,2'-lactone (racemic XVII-A), an oil, which has the following constants:

| I.R. | $\nu_{max}^{CHCl_3}$ | 1780, 1715 cm$^{-1}$; |
|---|---|---|
| N.M.R. | $\delta_{TMS}^{CDCL_3}$ | 0.90 (t, 3H); 1.1–3.3 (m, 16H); 4.66–5.0 p.p.m. (m, 1H). |

B. A mixture of 2.4 g. of dl [2'α-hydroxy-4'α,5'α-difluoromethylene-5'β-(3''-oxo-octan-1''-yl)cyclopent-1'α-yl]acetic acid 1,2'-lactone in 125 ml. of dry benzene containing 8.4 ml. of ethyleneglycol and 120 mg. of p-toluenesulfonic acid is refluxed under stirring for 20 hours using a Dean Stark trap to separate the water formed. It is then cooled, 20 ml. of a 10% solution of sodium bicarbonate is added, the organic phase separated and the aqueous phase extracted with benzene. The combined extracts are washed twice, dried over anhydrous magnesium sulfate and evaporated to dryness under reduced pressure to afford 2.62 g. of dl [2'α-hydroxy-4'α,5'α-difluoromethylene-5'β-(3''-ethylenedioxyoctan-1''-yl)cyclopent-1'α-yl]acetic acid 1,2'-lactone (racemic XVIII-A), an oil, which has the following constants:

| I.R. | $\nu_{max}^{CHCl_3}$ | 1780 cm$^{-1}$; |
|---|---|---|
| N.M.R. | $\delta_{TMS}^{CDCl_3}$ | 0.83 (t, 3H); 1.06–3.5 (m, 16H); 3.83 (s, 4H); 4.9–5.2 p.p.m. (m, 1H). |

C. A solution of 1.22 g. of diisobutyl aluminum hydride in toluene is added in a dropwise fashion to a stirred solution of 1.45 g. of crude dl [2'α-hydroxy-4'α,5'α-difluoromethylene-5'β-(3''-ethylenedioxyoctan-1''-yl) cyclopent-1'α-yl]acetic acid 1,2'-lactone in 50 ml. of anhydrous toluene previously cooled to −70° C. The reaction mixture is stirred for 5 minutes at said temperature, and quenched by the addition of methanol until gas evolution ceases. The resulting mixture is stirred for 15 minutes at room temperature, diluted with 75 ml. of ethyl acetate and filtered through a pad of magnesium sulfate. Evaporation of the filtrate under vacuum affords 1.42 g. of crude dl [2'α-hydroxy-4'α,-5'α-difluoromethylene-5'β-(3''-ethylenedioxyoctan-1''-yl)cyclopent-1'α-yl]acetaldehyde 1,2'-hemiacetal (racemic XIX-A), an oil, having the following constants:

| I.R. | $\nu_{max}^{CHCl_3}$ | 3425 cm$^{-1}$; |
|---|---|---|
| N.M.R. | $\delta_{TMS}^{CDCl_3}$ | 0.86 (t, 3H); 1.03–2.66 (m, 16H); 2.16–2.5 (m, 1H); 3.86 (s, 4H); 4.26–4.66 p.p.m. (m, 1H). |

In a similar manner, starting from dl [2'α-hydroxy-4'β,5'β-difluoromethylene-5'α-(3''-oxo-oct-1''(t)-en-1''-yl)cyclopent-1'α-yl]acetic acid 1,2'-lactone there are successively obtained:

dl [2'α-hydroxy-4'β,5'β-difluoromethylene-5'α-(3''-oxo-octan-1''-yl)cyclopent-1'α-yl]acetic acid 1,2'-lactone (racemic XVII-B), dl [2'α-hydroxy-4'β,5'β-difluoromethylene-5'α-(3''-ethylenedioxyoctan-1''-yl)cyclopent-1'α-yl]acetic acid 1,2'-lactone (racemic XVIII-B) and dl [2'α-hydroxy-4'β,5'β-difluoromethylene-5'α-(3''-ethylenedioxyoctan-1''-yl)cyclopent-1'α-yl]acetaldehyde 1,2'-hemiacetal (racemic XIX-B).

EXAMPLE 9

Finely powdered 5-triphenylphosphoniopentanoic acid (4.52 g.) is dried for 2 hours (75° C/0.1 mm) and dissolved in 8 ml. of anhydrous dimethyl sulfoxide, under argon atmosphere. To the solution thus obtained is added 9.71 ml. of 2M potassium methylsulfinyl carbanide in dimethyl sulfoxide, under stirring, to yield a red solution, which is stirred for 5 minutes. A solution of 1.4 g. of crude dl [2'α-hydroxy-4'α,5'α-difluoromethylene-5'β-(3''-ethylenedioxyoctan-1''-yl)cyclopent-1'α-yl]acetaldehyde 1,2'-hemiacetal in 5 ml. of dimethyl sulfoxide is then added, and the reaction mixture is stirred at room temperature for 3 hours. It is then diluted with 75 ml. of water and extracted four times with 50 ml. portions of ethyl acetate-ether (1:1) to remove the neutral components. The aqueous phase is then acidified with oxalic acid to pH∼5 and extracted with a (1:1) pentane-ether mixture (5 × 50 ml.). The acidic extracts are washed with 25 ml. of saturated sodium chloride solution, dried over anhydrous magnesium sulfate and evaporated to dryness under reduced pressure, to yield dl 9α-hydroxy-11α,1-2α-difluoromethylene-15-ethylenedioxyprost-5-cis-enoic acid (racemic XX-A) which is immediately treated with 50 ml. of ethereal diazomethane solution. The reaction mixture is kept for 15 minutes at room temperature and then evaporated to dryness under reduced pressure. Purification of the residue by t.l.c. using hexane-ethyl acetate (1:1) as eluant, affords the pure dl 9α-hydroxy-11α,12α-difluoromethylene-15-ethylenedioxyprost-5-cis-enoic acid methyl ester (racemic XXI-A), an oil, having the following constants:

| I.R. | | $\nu_{max}^{CHCl_3}$ | 3500, 1720 cm$^{-1}$ |
|---|---|---|---|
| N.M.R. | $\delta \, _{TMS}^{CDCl_3}$ | | 0.9 (t, 3H); 1.1–2.53 (m, 22H); 1.7 (m, 1H); 3.66 (s, 3H); 3.9 (s, 4H); 4.16–4.66 (m, 1H); 5.28–5.6 p.p.m. (m, 2H). |

By the same method but using 2 g. of dl [2'α-hydroxy-4'β,5'β-difluoromethylene-5'α-(3''-ethylenedioxyoctan-1''-yl)cyclopent-1'α-yl]acetaldehyde 1,2'-hemiacetal as starting material, there is obtained dl 9α-hydroxy-11β,12β-difluoromethylene-15-ethylenedioxy-12α-prost-5-cis-enoic acid methyl ester (racemic XXI-B), which is pruified by t.l.c. using hexane-ethyl acetate (70:30) as eluant.

EXAMPLE 10

A. To a solution of 325 mg of dl 9α-hydroxy-11α,1-2α-difluoromethylene-15-ethylenedioxyprost-5-cis-enoic acid methyl ester in 8 ml. of dimethoxyethane are added 2 micro drops of a 5% solution of cupric sulfate in 30% perchloric acid. The reaction mixture is stirred for 30 minutes at room temperature, 10 ml. of 10% aqueous sodium bicarbonate solution are added and the product extracted with ethyl acetate (3 × 20 ml.). The combined extracts are washed with water, dried over anhydrous magnesium sulfate and evaporated to dryness under reduced pressure. Purification of the residue by t.l.c. using methylene chloride-methanol (98:2) as eluant affords 250 mg. of pure dl 9α-hydroxy-11α,12α-difluoromethylene-15-ketoprost-5-cis-enoic acid methyl ester (racemic XXII-A), an oil, having the following constants:

| I.R. | | $\nu_{max}^{CHCl_3}$ | 3500, 1735, 1720 cm$^{-1}$ |
|---|---|---|---|
| N.M.R. | $\delta \, _{TMS}^{CDCl_3}$ | | 0.9 (t, 3H); 1.16–3.0 (m, 22-H); 3.66 (s, 3H); 4.1–4.46 (m, 1H); 5.33–5.6 p.p.m. (m, 2H). |

B. A stirred solution of 250 mg. (0.62 mmol) of dl 9α-hydroxy-11α,12α-difluoromethylene-15-ketoprost-5-cis-enoic acid methyl ester in 15 ml. of anhydrous tetrahydrofuran, cooled to −40° C is treated dropwise with 4.5 molar equivalents of methylmagnesium bromide (in the form of a 4N ethereal solution) following the course of the reaction by t.l.c. analysis [hexane-ethyl acetate (1:1)]. After 2 hours at −40° C there are added 1.5 additional molar equivalents of the reagent, and the reaction mixture maintained under the same conditions for 1 hour further, followed by the addition of 5 ml. of methanol and thereafter 30 ml. of ethyl acetate. The resulting mixture is washed with saturated sodium chloride solution, dried over anhydrous magnesium sulfate and evaporated to dryness under reduced pressure. Purification of the residue by t.l.c., using hexane-ethyl acetate (1:1) as gradient, affords 75 mg. of dl 9α,15 ⟨-dihydroxy-11α,12α-difluoromethylene-15 ⟩-methylprost-5-cis-enoic acid methyl ester (racemic XXIII-A), an oil, having the following constants:

| I.R. | | $\nu_{max}^{CHCl_3}$ | 3500, 1730 cm$^{-1}$; |
|---|---|---|---|
| N.M.R. | $\delta \, _{TMS}^{CDCl_3}$ | | 0.88 (t, 3H); 1.13 (s, 3H); 1.2–2.7 (m, 22H), 1.5–1.68 (m, 2H); 3.66 (s, 3H); 4.2–4.4 (m, 1H); 5.41–5.53 p.p.m. (m, 2H); |
| M.S. (as ditrimethylsilyl ether) 545 (M$^+$ —CH$_3$) | | | |

By repeating the procedures of this Example using dl 9α-hydroxy-11β,12β-difluoromethylene-15-ethylenedioxy-12α-prost-5-cis-enoic acid as starting material there are successively obtained dl 9α-hydroxy-11β,12β-difluoromethylene-15-keto-12α-prost-5-cis-enoic acid methyl ester (racemic XXII-B) and dl 9α,15 ⟨-dihydroxy-11β,12β-difluoromethylene-15 ⟩-methyl-12α-prost-5-cis-enoic acid methyl ester (racemic XXIII-B), an oil, which has the following constants:

| I.R. | | $\nu_{max}^{CHCl_3}$ | 3500, 1730 cm$^{-1}$; |
|---|---|---|---|
| N.M.R. | $\delta \, _{TMS}^{CDCl_3}$ | | 0.88 (t, 3H); 1.14 (s, 3H); 1.2–2.5 (m, 22H); 1.65 (m, 2H); 3.65 (s, 3H); 4.16–4.32 (m, 1H); 5.35–5.54 p.p.m. (m, 2H); |
| M.S. (as ditrimethylsilyl ether) 545 (M$^+$ —CH$_3$). | | | |

EXAMPLE 11

To a stirred mixture of 2.5 g. of chromium trioxide-dipyridine complex [prepared as described by J. C. Collins et al., *Tetrahedron Letters* 39, 3363 (1968)], 5 g. of Celite, diatomaceous earth, and 15 ml. of anhydrous methylene chloride, cooled to 0° C. is added a solution of 570 mg. of dl 9α,15 ⟨-dihydroxy-11α,12α-difluoromethylene-15 ⟩-methylprost-5-cis-enoic acid methyl ester in 30 ml. of anhydrous methylene chloride, and the resulting mixture is stirred at 0° C for 20 additional minutes; 5.0 g. of sodium hydrogen sulfate monohydrate are then added, and the mixture is stirred for 10 minutes further and filtered through a pad of magnesium sulfate, washing the solid material with methylene chloride. The combined filtrates are evaporated to dryness under reduced pressure and the residue purified by t.l.c. using ethyl acetate-hexane (1:1) as eluant, thus obtaining 240 mg. of dl 9-keto-11α,12α-difluoromethylene-15 ⟨-hydroxy-15 ⟩-methylprost-5-cis-enoic acid methyl ester (racemic XXIV-A), an oil, having the following constants:

| I.R. | | $\nu_{max}^{CHCl_3}$ | 3500, 1745 cm$^{-1}$; |
|---|---|---|---|
| | CDCl$_3$ | | |

| | | |
|---|---|---|
| N.M.R. | δ TMS | 0.88 (t, 3H); 1.15 (s, 3H); 1.22–2.9 (m, 22H); 1.61–1.69 (m, 1H); 3.64 (s, 3H); 5.38–5.6 p.p.m. (m, 2H); |
| M.S. (as ditrimethylsilyl ether, 9-trimethylsilyl enol ether) 538 (M$^+$ —HF). | | |

By the same method, starting from dl 9α,15 -dihydroxy-11β,12β-difluoromethylene-15 } -methyl-12α-prost-5-cis-enoic acid methyl ester there is obtained dl 9-keto-11β,12β-difluoromethylene-15 } -hydroxy-15 } -methyl-12α-prost-5-cis-enoic acid methyl ester (racemic XXIV-B), an oil, having the following constants:

| | | |
|---|---|---|
| I.R. | $\nu$ CHCl$_3$ max | 3500, 1745 cm$^{-1}$; |
| N.M.R. | δ CDCl$_3$ TMS | 0.88 (t, 3H); 1.15, 1.18 (singlets 3H); 1.2–2.6 (m, 22H); 1.45–1.75 (m, 1H); 3.64 (s, 3H); 5.36–5.54 p.p.m. (m, 2H); |
| M.S. | | 399 (M$^+$ —CH$_3$). |

EXAMPLE 12

To a solution of 100 mg. of dl 9α,15 } -dihydroxy-11α,12α-difluoromethylene-15 } -methylprost-5-cis-enoic acid methyl ester in 2 ml. of methanol is added a solution of 150 mg. of anhydrous potassium carbonate in 0.6 ml. of water, maintaining the reaction mixture at room temperature for 44 hours. It is then evaporated under vacuum to one half the original volume and diluted with 10 ml. of water. Extraction with methylene chloride removes the neutral impurities. The aqueous phase is acidified with oxalic acid to pH~6 and extracted with ethyl acetate. The combined organic extract is washed with saturated sodium chloride solution, dried over anhydrous magnesium sulfate and evaporated to dryness under vacuum, thus yielding 87 mg. of dl 9α,15 } -dihydroxy-11α,12α-difluoromethylene-15 } -methylprost-5-cis-enoic acid (racemic XXV-A), an oil, having the following constants:

| | | |
|---|---|---|
| I.R. | $\nu$ CHCl$_3$ max | 3430, 1715 cm$^{-1}$; |
| N.M.R. | δ CDCl$_3$ TMS | 0.9 (t, 3H); 1.16 (s, 3H); 1.23–2.66 (m, 22H); 4.0–5.0 (m, 4H); 5.0–5.83 p.p.m. (m, 2H). |

In a similar manner dl 9α,15 } -dihydroxy-11β,12β-difluoromethylene-15 } -methyl-12α-prost-5-cis-enoic acid methyl ester is converted into dl 9α,15 } -dihydroxy-11β,12β-difluoromethylene-15 } methyl-12α-prost-5-cis-enoic acid (racemic XXV-B).

EXAMPLE 13

A. to a prehydrogenated suspension of 45 mg. of 5% palladium-charcoal catalyst in 15 ml. of ethyl acetate is added a solution of 437 mg. of dl 9α-hydroxy-11α,12α-difluoromethylene-15-ethylenedioxyprost-5-cis-enoic acid methyl ester in 15 ml. of ethyl acetate and the resulting mixture is stirred under an atmosphere of hydrogen until the absorption of hydrogen ceases. The catalyst is then separated by filtration and washed with ethyl acetate. The combined filtrates are evaporated to dryness under reduced pressure to yield 435 mg. of dl 9α-hydroxy-11α,12α-difluoromethylene-15-ethylenedioxyprostanoic acid methyl ester (racemic XXVI-A), an oil, which has the following constants:

| | | |
|---|---|---|
| I.R. | $\nu$ CHCl$_3$ max | 3500, 1735 cm$^{-1}$; |
| N.M.R. | δ CDCl$_3$ TMS | 0.86 (t, 3H); 1.06–2.6 (m, 26H); 3.6 (s, 3H); 3.86 (s, 4H); 4.04–4.46 p.p.m. (m, 1H). |

B. Three micro drops of a 5% cupric sulfate solution in 30% perchloric acid are added to a stirred solution of 435 mg. of dl 9α-hydroxy-11α,12α-difluoromethylene-15-ethylenedioxyprostanoic acid methyl ester in 12 ml. of dimethoxyethane. The reaction mixture is kept for 18 hours at room temperature, diluted with 10 ml. of 10% sodium bicarbonate solution and extracted with ethyl acetate. The organic extract is washed with saturated sodium chloride solution, dried over anhydrous magnesium sulfate and evaporated to dryness under vacuum, to produce 389 mg. of dl 9α-hydroxy-11α,12α-difluoromethylene-15-keto-prostanoic acid methyl ester (racemic XXVII-A), an oil, having the following constants:

| | | |
|---|---|---|
| I.R. N.M.R. | δ CDCl$_3$ TMS | $\nu$ CHCl$_3$ MAX 3440, 1735, 1715 cm$^{-1}$; 0.86 (t, 3H); 1.03–2.76 (m, 26H); 3.60 (s, 3H); 4.0–4.4 p.p.m. (m, 1H). |

C. A stirred solution of 360 mg. of dl 9α-hydroxy-11α,12α-difluoromethylene-15-keto-prostanoic acid methyl ester in 30 ml. of anhydrous tetrahydrofuran is cooled to −40° C and treated dropwise with 1.5 molar equivalents of methylmagnesium bromide (using a 4N ethereal solution). The course of the reaction is followed by t.l.c. analysis [hexane-ethyl acetate (1:1)]. After 2 hours, an additional portion of 1.5 molar equivalents of methylmagnesium bromide is added, and thereafter two additional portions of 1.5 molar equivalents of the reagent are added at 20 minute intervals. When the reaction appears to be substantially complete the excess reagent is destroyed by the addition of 3 ml. of methanol and then diluted with 15 ml. of ethyl acetate. The resultant solution is washed with saturated sodium chloride solution, dried over anhydrous magnesium sulfate and evaporated to dryness under reduced pressure.

The residue is purified by t.l.c. using hexane-ethyl acetate (1:1) as eluant, thus obtaining 187 mg. of dl 9α,15 }-dihydroxy-11α,12α-difluoromethylene-15 }-methylprostanoic acid methyl ester (racemic XXVIII-A), an oil, which has the following constants:

| I.R. | $\nu_{max}^{CHCl_3}$ | 3500,1735 cm$^{-1}$; |
|---|---|---|
| N.M.R. | $\delta_{TMS}^{CDCl_3}$ | 0.88 (t,3H);1.15(s,3H); 1.2–2.8 (m, 26H); 1.65–2.16 (m, 2H); 3.63 (s, 3H); 4.1–4.4 p.p.m. (m, 1H); |
| M.S. | | 382 (M$^+$−2H$_2$O). |

By repeating the procedures described in parts A and B, using dl 9α-hydroxy-11β,12β-difluoromethylene-15-ethylenedioxy-12α-prost-5-cis-enoic acid methyl ester as starting material there are successively obtained dl 9α-hydroxy-11β,12β-difluoromethylene-15-ethylenedioxy-12α-prostanoic acid methyl ester and dl 9α-hydroxy-11β,12β-difluoromethylene-15-keto-12α-prostanoic acid methyl ester. The latter compound is then alkylated with methylmagnesium bromide, in accordance with the method of part C of this Example but using 8 molar equivalents of the reagent, to produce dl 9α,15 }-dihydroxy-11β,12β-difluoromethylene-15 }-methyl-12α-prostanoic acid methyl ester (racemic XXVIII-B), an oil, having the following constants:

| I.R. | $\nu_{max}^{CHCl_3}$ | 3480, 1730 cm$^{-1}$; |
|---|---|---|
| N.M.R. | $\delta_{TMS}^{CDCl_3}$ | 0.87 (t, 3H); 1.13 (s, 3H); 1.22–2.60 (m, 26H); 1.46–1.77 (m, 2H); 3.63 (s, 3H); 4.1–4.33 p.p.m. (m, 1H); |
| M.S. | | (as ditrimethylsilyl ether) 547 (M$^+$ −CH$_3$). |

EXAMPLE 14

A mixture of 1.12 g. of chromium trioxidedipyridine complex, 2.24 g. of Celite, diatomaceous earth, and 35 ml. of anhydrous methylene chloride is cooled to 0° C. To this stirred, cooled mixture is added a solution of 225 mg. of dl 9α,15 }-dihydroxy-11α,12α-difluoromethylene-15 }-methylprostanoic acid methyl ester in 10 ml. of methylene chloride, stirring the reaction mixture for 20 minutes at 0° C., 2.24 g. of sodium hydrogen sulfate monohydrate are then added and the mixture stirred for 10 additional minutes and filtered trhough a pad of magnesium sulfate. The solid material is washed well with methylene chloride and the combined filtrates are evaporated under vacuum. The oily residue is purified by preparative thin layer chromatography using hexane-ethyl acetate (1:1) as eluant, to afford 170 mg. of pure dl 9-keto-11α,12α-difluoromethylene-15 }-hydroxy-15 }-methylprostanoic acid methyl ester (racemic XXIX-A), an oil, which has the following constants:

| I.R. | $\nu_{max}^{CHCl_3}$ | 3500, 1745, 1735 cm$^{-1}$; |
|---|---|---|
| N.M.R. | $\delta_{TMS}^{CDCl_3}$ | 0.88 (t, 3H); 1.17 (s, 3H); 1.22–2.76 (m, 26H); 3.65 p.p.m. (s, 3H); |
| M.S. | | 416 (M$^+$). |

In a similar manner, dl 9α,15 }-dihydroxy-11β,12β-difluoromethylene-15 }-methyl-12α-prostanoic acid methyl ester is converted into dl 9-keto-11β,12β-difluoromethylene-15 }-hydroxy-15 }-methyl-12α-prostanoic acid methyl ester (racemix XXIX-B), an oil, having the following constants:

| I.R. | $\nu_{max}^{CHCl_3}$ | 3500, 1745, 1730 cm$^{-1}$; |
|---|---|---|
| N.M.R. | $\delta_{TMS}^{CDCl_3}$ | 0.88 (t, 3H); 1.15, 1.17 (singlets, 3H); 1.22–2.7 (m, 26H); 1.48–1.68 (m, 1H); 3.64 p.p.m. (s, 3H); |
| M.S. | (as the O-methyloxime, trimethylsilyl ether) 502 (M$^+$ −CH$_3$). | |

EXAMPLE 15

One hundred milligrams of dl 9α,15 }-dihydroxy-11α,12α-difluoromethylene-15 }-methylprostanoic acid methyl ester are dissolved in a mixture of 2 ml. of methanol, 0.6 ml. of water and 150 mg. of anhydrous potassium carbonate. The reaction mixture is maintained at room temperature for 26 hours and then evaporated under reduced pressure to one-half the original volume, diluted with 10 ml. of water and extracted with methylene chloride to remove the neutral impurities. The aqueous phase is acidified with oxalic acid to pH~6 and extracted with ethyl acetate. The acidic extract is washed with saturated sodium chloride solution and evaporated to dryness under vacuum, thus obtaining 89 mg. of dl 9α,15 }-dihydroxy-11α,12α-difluoromethylene-15 }-methylprostanoic acid (racemic XXX-A), an oil, which has the following constants:

| I.R. | $\nu_{max}^{CHCl_3}$ | 3440, 1720 cm$^{-1}$; |
|---|---|---|
| N.M.R. | $\delta_{TMS}^{CDCl_3}$ | 0.86 (t, 3H); 1.13 (s, 3H); 1.2–2.83 (m, 26H); 4.0–5.0 p.p.m. (m, 4H). |

By the same method dl 9α,15 }-dihydroxy-11β,12β-difluoromethylene-15 }-methyl-12α-prostanoic acid methyl ester is converted into dl 9α,15 }-dihydroxy-11β,12β-difluoromethylene-15 }-methyl-12α-prostanoic acid (racemic XXX-B).

EXAMPLE 16

In accordance with the method of Example 14, dl 9α,15 }-dihydroxy-11α,12α-difluoromethylene-15 }-methylprostanoic acid is oxidized with chromium trioxide-dipyridine complex, to produce dl 9-keto-11α,12α-difluoromethylene-15 }-hydroxy-15 }-methylprostanoic acid (racemic XXXII-A).

Likewise, starting from dl 9α,15 }-dihydroxy-11α,12α-difluoromethylene-15 }-methylprost-5-cis-enoic acid and dl 9α,15 }-dihydroxy-11β,12β-difluoromethylene-15 }-methyl-12α-prost-5-cis-enoic acid there are respectively obtained dl 9-keto-11α,12α-difluoromethylene-15 }-hydroxy-15 }-methylprost-5-cis-enoic acid (racemic XXXI-A) and dl 9 -keto- 11β,12β-difluoromethylene-15∤-hydroxy-15∤-methyl-12α-prost-5-cis-enoic acid (racemic XXXI-B).

EXAMPLE 17

To a solution of 100 mg. of dl 9-keto-11α,12α-difluoromethylene-15α-hydroxyprost-5-cis-enoic acid in 10 ml. of methylene chloride is added 1 ml. of an ethereal solution of diazomethane, maintaining the reaction mixture at room temperature for 15 minutes. It is then evaporated under reduced pressure, to produce dl 9-keto-11α,12α-difluoromethylene-15α-hydroxyprost-5-cis-enoic acid methyl ester.

Likewise dl 9-keto-11α,12α-difluoromethyl ene-15β-hydroxyprost-5-cis-enoic acid and dl 9-keto-11β, 12β-difluoromethylene-15α-hydroxy-12α-prost-5-cis-enoic acid are converted into the corresponding methyl esters.

EXAMPLE 18

By following the methods of Example 3, parts A and B and the condensation method of Example 4, 1'S-2'α-hydroxy-4'α, 5'α-difluoromethylene-5'α-(3''α-hydroxyoct-1'''(t)-en-1'''-yl)cyclopent-1'α-yl]acetic acid 1,2'-lactone is converted successively into 1'S-[2'α-hydroxy-4'α,5'α-difluoromethylene-5'β-(3''α-hydroxyoctan-1'''-yl)cyclopent-1'α-yl]acetic acid 1,2'-lactone, 1'S-[2'α-hydroxy-4'α,5'α-difluoromethylene-5'β-(3''α-hydroxyoctan-1'''-yl)cyclopent-1'α-yl]acetaldehyde 1,2'-hemiacetal and 8S-11α, 12α-difluoromethylene-9α,15α-dihydroxyprost-5-cis-enoic acid (8S-antimer of VII-A).

Likewise, starting from 1'S-[2'α-hydroxy-4'α,5'α-difluoromethylene-5'α-(3''α-hydroxyoct-1'''(t)-en-1'''-yl) cyclopent-1'α-yl]acetic acid 1,2'-lactone, 1'S-[2'α-hydroxy-4'α,5'α-difluoromethylene-5'β-(3''β-hydroxyoct-1'''(t)-en-1'''-yl) cyclopent-1'α-yl]acetic acid 1,2'-lactone and 1'S-[2'α-hydroxy-4'β,5'β-difluoromethylene-5'α-(3''β-hydroxyoct-1'''(t)-en-1'''-yl)cyclopent-1'α-yl]acetic acid 1,2'-lactone there are obtained as final products, respectively:

8S-11β,12β-difluoromethylene-9α,15α-dihydroxy-12α-prost-5-cis-enoic acid, 8S-11α,12α-difluoromethylene-9α,15β-dihydroxyprost-5-cis-enoic acid and 8S-11β,12β-difluoromethylene-9α,15β-dihydroxy-12α-prost-5-cis-enoic acid.

Upon reaction of the above mentioned prostenoic acid compounds with diazomethane there are obtained the corresponding methyl esters.

EXAMPLE 19

In accordance with the hydrogenation method of Example 5, 8S-11α,12α-difluoromethylene-9α,15α-dihydroxyprost-5-cis-enoic acid is converted into 8S-11α,12α-dilfluoromethylene-9α,15α-dihydroxyprostanoic acid (8S-antimer of IX-A).

Likewise, from the remaining prost-5-cis-enoic acid compounds obtained in Example 16 there are respectively obtained:

8S-11β,12β-difluoromethylene-9α,15α-dihydroxy-12α-prostanoic acid, 8S-11α,12α-difluoromethylene-9α,15β-dihydroxyprostanoic acid and 8S-11β,12β-difluoromethylene-9α,15β-dihydroxy-12α-prostanoic acid, as well as the corresponding methyl esters.

EXAMPLE 20

Example 6 is replaced using 1'S-[2'α-hydroxy-4'α,5'α-difluoromethylene-5'β-(3'α-hydroxyoctan-1''-yl)cyclopent-1'α-yl]acetic acid 1,2'-lactone as starting material to produce successively:

1'S-[2'α-hydroxy-4'α,5'α-difluoromethylene-5'β-(3''α-tetrahydropyranyloxyoctan-1'''-yl)cyclopent-1'α-yl]acetic acid 1,2'-lactone (1'S-antimer of XI-A).

1'S-[2'α-hydroxy-4'α,5'α-difluoromethylene-5'β-(3''α-tetrahydropyranyloxyoctan-1'''-yl)cyclopent-1'α-yl]acetaldehyde 1,2'-hemiacetal (1'S-antimer of XII-A), 8S-11α,12α-difluoromethylene-9α-hydroxy-15α-tetrahydropyranyloxyprost-5-cis-enoic acid (8S-antimer of XIII-A), 8R-9-keto-11α,12α-difluoromethylene-15α-tetrahydropyranyloxyprost-5-cis-enoic acid (8R-antimer of XIV-A), and 8R-9-keto-11α,12α-difluoromethylene-15α-hydroxyprost-5-cis-enoic acid (8R-antimer of XV-A).

Likewise but using 1'S-[2'α-hydroxy-4'β,5'α-difluoromethylene-5'α-(3''α-hydroxyoctan-1'''-yl)cyclopent-1'α-yl]acetic acid 1,2'-acetone, 1'S-[2'α-hydroxy-4'α,5'α-difluoromethylene-5'β-(3''β-hydroxyoctan-1'''-yl)cyclopent-1'α-yl]acetic acid 1,2'-lactone and 1'S-[2'α-hydroxy-4'β,5'β-difluoromethylene-5'α-(3''β-hydroxyoctan-1'''-yl)cyclopent-1'α-yl]acetic acid 1,2'-lactone there are produced as final products:

8R-9-keto-11β,12β-difluoromethylene-15α-hydroxyprost-5-cis-enoic acid, 8R-9-keto-11α,12α-difluoromethylene-15β-hydroxyprost-5-cis-enoic acid and 8R-9-keto-11β,12β-difluoromethylene-15β-hydroxy-12α-prost-5-cis-enoic acid.

EXAMPLE 21

By repeating the methods of Examples 8, 9 and 10, using 1'S-[2'α-hydroxy-4'α,5'α-difluoromethylene-5'β-(3''-oxo-oct-1'''(t)-en-1'''-yl)cyclopent-1'α-yl]acetic acid 1,2'-lactone as starting material there are successively obtained:

1'S-[2'α-hydroxy-4'α,5'α-difluoromethylene-5'α(-3''-oxo-octan-1'''-yl)cyclopent-1'α-yl]acetic acid 1,2'-lactone (1'S-antimer of XVII-A).

1'S-[2'α-hydroxy-4'α,5'α-difluoromethylene-5'α(-3''-ethylenedioxyoctan-1'''-yl)cyclopent-1'α-yl]acetic acid 1,2'-lactone (1'S-antimer of XVIII-A), 1'S-[2'α-hydroxy-4'α,5'α-difluoromethylene-5'β-(3''-ethylenedioxyoctan-1'''-yl)cyclopent-1'α-yl]acetaldehyde 1,2'-hemiacetal (1'S-antimer of XIX-A), 8S-9α-hydroxy-11α,12α-difluoromethylene-15-ethylenedioxyprost-5-cis-enoic acid (8S-antimer of XX-A), 8S-9α-hydroxy-11α,12α-difluoromethylene-15-ethylenedioxyprost-5-cis-enoic acid methyl ester (8S-antimer of XXI-A), 8S-9α-hydroxy-11α,12α-difluoromethylene-15-ketoprost-5-cis-enoic acid methyl ester (8S-antimer of XXII-A), and 8S-9α,15∤-hydroxy-11α,12α-difluoromethylene-15∤-methylprost-5-cis-enoic acid methyl ester (8S-antimer of XXIII-A).

In a similar manner, but using 1'S-[2'α-hydroxy-4'β,5'β-difluoromethylene-5'α-(3'''-oxo-oct-1'''(t)-en-1'''-yl)cyclopent-1'α-yl]acetic acid 1,2'-lactone as starting material there is produced 8S-9α,15∤-dihydroxy- 11β,12β-difluoromethylene-15{-methyl-12α-prost-5-cis-enoic acid methyl ester as final product.

Hydrolysis of the methyl ester group with potassium carbonate, in accordance with the method of Example 12 gives rise to the corresponding free acids, namely 8S-9α,15 -dihydroxy-11α,12α-difluoromethylene-15 -methylprost-5-cis-enoic acid and 8S-9α,15}-dihydroxy-11β,12β-difluoromethylene-15{-methyl-12α-prost-5-cis-enoic acid.

EXAMPLE 22

In accordance with the method of Example 11, 8S-9α,15{-dihydroxy-11α,12α-difluoromethylene-15{-methylprost-5-cis-enoic acid methyl ester is oxidized with chromium trioxide-dipyridine complex, to produce 8R-9-keto-11α,12α-difluoromethylene-15{-hydroxy-15{-methylprost-5-cis-enoic acid methyl ester (8R-antimer of XXIV-A).

Likewise 8S-9α,15 -dihydroxy-11β,12β-difluoromethylene-15{-methyl-12α-prost-5-cis-enoic acid methyl ester is converted into 8R-9-keto-11β,12β-difluoromethylene-15} -hydroxy-15 \-methyl-12β-prost-5-cis-enoic acid methyl ester.

EXAMPLE 23

By following the procedures of Example 13 using 8S-9α-hydroxy-11α,12α-difluoromethylene-15-ethylenedioxyprost-5-cis-enoic acid methyl ester as starting material there are successively obtained:

8S-9α-hydroxy-11α,12α-difluoromethylene-15-ethylenedioxyprostanoic acid methyl ester (8S-antimer of XXVI-A), 8S-9α-hydroxy-11α,12α-difluoromethylene-15-ketoprostanoic acid methyl ester (8S-antimer of XXVII-A) and 8S-9α,15}-dihydroxy-11α,12α-difluoromethylene-15}-methylprostanoic acid methyl ester (8S-antimer of XXVIII-A).

Upon saponification of the latter compound with potassium carbonate, in accordance with the method of Example 15, there is obtained 8S-9α,15{-dihydroxy-11α,12α-difluoromethylene-15}-methylprostanoic acid (8S-antimer of XXX-A).

Likewise, starting from 8S-9α-hydroxy-11β,12β-difluoromethylene-15-ethylenedioxy-12α-prost-5-cis-enoic acid methyl ester there is obtained 8S-9α,15}-dihydroxy-11β,12β-difluoromethylene-15} -methyl-12α-prostanoic acid, via its methyl ester.

EXAMPLE 24

Example 11 is repeated using 8S-9α,15} -dihydroxy-11α,12α-difluoromethylene-15} -methylprostanoic acid methyl ester and 8S-9α,15} -dihydroxy-11β,12β-difluoromethylene-15{ -methyl-12α-prostanoic acid methyl ester as starting materials, to produce 8R-9-keto-11α,12α-difluoromethylene-15} -hydroxy-15} -methylprostanoic acid methyl ester and 8R-9-keto-11β,12β-difluoromethylene-15{ -hydroxy-15} -methyl-12α-prostanoic acid methyl ester, respectively.

EXAMPLE 25

To a solution of 100 mg. of dl 9-keto-11α,12α-difluoromethylene-15α-hydroxyprostanoic acid in 5 ml. of ether is added 1 ml. of an ethereal solution of diazoethane, and the reaction mixture is maintained at room temperature for 10 minutes. The solvents and excess reagent are eliminated by vacuum distillation and the residue is purified by t.l.c. to afford dl 9-keto-11α,12α-difluoromethylene-15α-hydroxyprostanoic acid ethyl ester.

In a similar manner but using diazopropane in place of diazoethane, the propyl ester of dl 9-keto-11α,12α-difluoromethylene-15α-hydroxyprostanoic acid is obtained.

By the same method the free racemic and antimeric prostanoic and prostenoic acid derivatives obtained in Examples 2, 4, 5, 6, 7, 12, 15, 16, 18 to 21 and 23 can be converted into the corresponding ethyl and propyl esters. Representative compounds thus obtained are:

dl 11β,12β-difluoromethylene-9α,15α-dihydroxy-12α-prostanoic acid ethyl ester, dl 9-keto-11β,12β-difluoromethylene-15α-hydroxy-12α-prostanoic acid propyl ester, dl 11α,12α-difluoromethylene-9α,15α-dihydroxyprost-5-cis-enoic acid ethyl ester, dl 11α,12α-difluoromethylene-9α,15β-dihydroxyprostanoic acid propyl ester, dl 9-keto-11α,12α-difluoromethylene-15α-hydroxyprost-5-cis-enoic acid ethyl ester, dl 9-keto-11β,12β-difluoromethylene-15β-hydroxy-12α-prost-5-cis-enoic acid propyl ester, dl 9α,15{-dihydroxy-11α,12α-difluoromethylene-15{-methylprost-5-cis-enoic acid propyl ester, dl 9α,15{-dihydroxy-11β,12β-difluoromethylene-15{-methyl-12α-prost-5-cis-enoic acid propyl ester, dl 9α,15{-dihydroxy-11α,12α-difluoromethylene-15{-methylprostanoic acid ethyl ester, dl 9α,15{-dihydroxy-11β,12β-difluoromethylene-15{-methyl-12α-prostanoic acid ethyl ester, as well as the ethyl and propyl esters of the corresponding antimeric compounds.

EXAMPLE 26

To a solution of 100 mg. of dl 9-keto-11α,12α-difluoromethylene-15α-hydroxyprostanoic acid in 10 ml. of methanol is added 2.75 ml. of a 0.1N solution of sodium hydroxide and the mixture is stirred at room temperature for 1 hour. It is then evaporated to dryness under reduced pressure, to give the sodium salt of dl 9-keto-11α,12α-difluoromethylene-15α-hydroxyprostanoic acid.

By employing 1.1 molar equivalents of potassium hydroxide (in the form of a 0.1N solution) in place of sodium hydroxide in the above procedure the potassium salt of dl 9-keto-11α,12α-difluoromethylene-15α-hydroxyprostanoic acid is obtained.

Similarly, the sodium and potassium salts of other prostanoic and 5-cis-prostenoic acid derivatives obtained in the previous Examples can be produced, e.g., sodium salt of dl 9-keto-11α,12α-difluoromethylene-15α-hydroxyprost-5-cis-enoic acid, sodium salt of dl 11α,12α-difluoromethylene-9α,15α-dihydroxyprost-5-cis-enoic acid, sodium salt of dl 9-keto-11β,12β-difluoromethylene-15α-hydroxy-12α-prosta-5-cis-enoic acid, potassium salt of dl 11α,12α-difluoromethylene-9α,15β-dihydroxyprostanoic acid, potassium salt of dl 9α,15{-dihydroxy-11α,12α-difluoromethylene-15{-methylprost-5-cis-enoic acid and potassium salt of dl 9α,15{-dihydroxy-11β,12β-difluoromethylene-15{-methylprostanoic acid as well as the salts of the corresponding antimeric compounds.

EXAMPLE 27

To a solution of 100 mg. of dl 11α,12α-difluoromethylene-9α,15α-dihydroxyprostanoic acid in 10 ml. of methanol is added a mixture of 1 ml. of concentrated ammonium hydroxide solution and 5 ml. of methanol. The resulting mixture is stirred for two hours at room temperature and then evaporated to dryness, to yield the ammonium salt of dl 11α,12α-difluoromethylene-9α,15α-dihydroxyprostanoic acid.

By employing dimethylene, diethylamine or dipropylamine in place of ammonium hydroxide in the above procedure, the corresponding salts of dl 11α,12α-difluoromethylene-9α,15α-dihydroxyprostanoic acid are obtained.

In a similar manner, the ammonium dimethylamine, diethylamine and dipropylamine salts of other racemic and antimeric prostanoic and prostenoic acid derivatives of the previous Examples can be prepared.

EXAMPLE 28

To a mixture of 67.3 mg. of procaine and 5 ml. of aqueous methanol is added 100 mg. of dl 9-keto-11α,12α-difluoromethylene-15α-hydroxyprost-5-cis-enoic acid in 5 ml. of methanol and the resultant reaction mixture is stirred at room temperature for 16 hours. It is then evaporated to dryness under reduced pressure to give the procaine salt of dl 9-keto-11α,12α-difluoromethylene-15α-hydroxyprosta-5-cis-enoic acid.

Similarly, the lysine, caffeine and arginine salts thereof are obtained

In like manner, the procaine, lysine, caffeine and arginine salts of other racemic and antimeric prostanoic and prostenoic acid derivatives obtained in the previous Examples can be produced e.g., the procaine salt of dl 11α,12α-difluoromethylene-9α,15α-dihydroxyprostanoic acid, the caffeine salt of dl 9-keto-11β,12β-difluoromethylene-15α-hydroxy-12α-prost-5-cis-enoic acid, the lysine salt of dl 9α,15 { -dihydroxy-11α,12α-difluoromethylene-15 } -methylprost-5-cis-enoic acid and the arginine salt of dl 9α,15 } -dihydroxy-11β,12β-difluoromethylene-15 } -methyl-12α-prostanoic acid, as well as the corresponding salts of the antimeric compounds.

EXAMPLE 29

Intravenous bronchodilator test in the guinea pig (histamine challenge).

| Test animal: | Female guinea pig, 400–500 g. |
|---|---|
| Vehicle: | Buffered saline. |

Procedure: The animals are anesthetized with urethane (1 g./Kg. intraperitoneally) and both the trachea and a jugular vein are cannulated. The tracheal cannula (plastic tube) is attached to a Harvard ventilator and pressure transducer to measure changes in respiratory resistance. The jugular cannula (a 22 gauge needle) permits injection of the intravenously administered materials. Recording is done via a Harvard Biograph. A standard histamine challange is given to determine the animal's sensitivity to histamine. Five minutes later the test material is given intravenously followed by a second histamine challange after dosing with the test material. Repeated histamine challanges are given to determine duration of action of the test material.

As measured by this assay, dl 9-keto-11α,12α-difluoromethylene-15α-hydroxyprostanoic acid has four times the activity of $PGE_2$, dl 9-keto-11α,12α-difluoromethylene-15α-hydroxyprost-5-cis-enoic acid has six times the activity of $PGE_2$ and dl 9-keto-11α,12α-difluoromethylene-15β-hydroxyprost-5-cis-enomic acid has greater than 10 times the activity of $PGE_2$.

What is claimed is:

1. A racemic or antimeric compound selected from the group of those represented by the formulas:

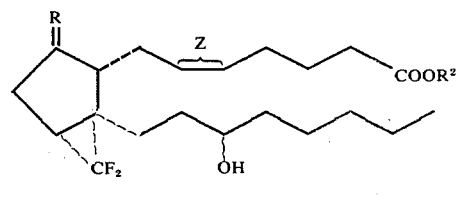

(A)

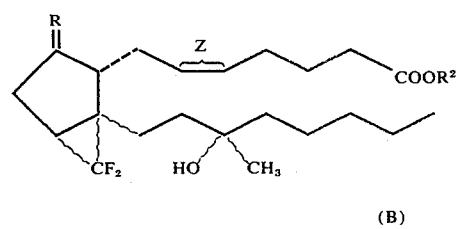

(B)

wherein

R is a keto group or α-hydroxy-β-hydrogen;

$R^2$ is hydrogen, a lower alkyl group or the non-toxic, pharmaceutically acceptable salts of compounds in which $R^2$ is hydrogen;

Z is a saturated linkage or a cis double bond and the wavy lines ( ) indicate the α or β configuration or mixtures thereof, provided that when the side chain attached at the C-12 position is β, the difluoromethylene group at the C-11,12 positions is 11α,12α only, and when the side chain attached at the C-12 position is α, the difluoromethylene group at the C-11,12 positions is 11β,12β only.

2. A compound according to claim 1 wherein R is keto.

3. A compound according to claim 1 wherein R is α-hydroxy-β-hydrogen.

4. A compound according to claim 1 wherein Z is a saturated linkage.

5. A compound according to claim 1 wherein Z is a cis double bond.

6. A compound according to claim 1 wherein said compound is a racemate.

7. A compound according to claim 1 wherein said compound is an antimeric compound.

8. A compound according to claim 1 formula (A).

9. The compounds of claim 8 wherein R is keto and the side chain attached at the C-12 position is β, represented by the formulas:

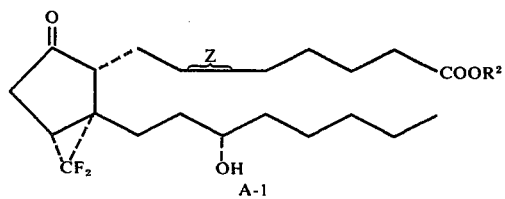
A-1

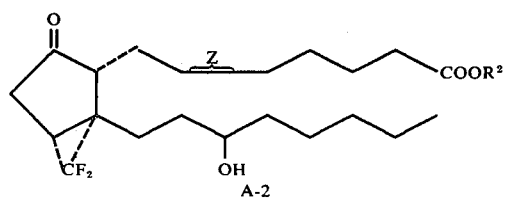
A-2

10. The compounds of claim 8 wherein R is α-hydroxy-β-hydrogen and the side chain attached to the C-12 position is β, represented by the formulas:

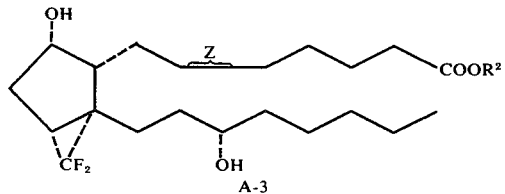
A-3

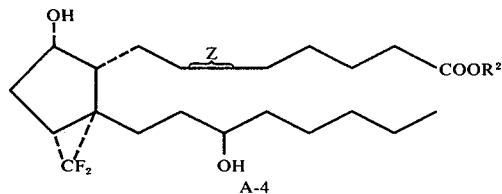
A-4

11. The compounds of claim 8 wherein R is keto and the side chain attached to the C-12 position is α, represented by the formulas:

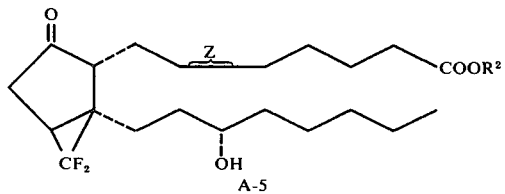
A-5

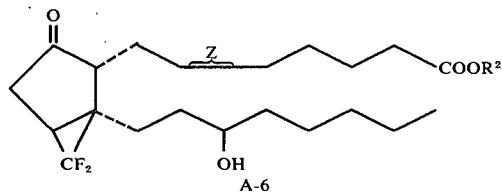
A-6

12. The compounds of claim 8 wherein R is α-hydroxy-β-hydrogen and the side chain attached to the C-12 position is α, represented by the formulas:

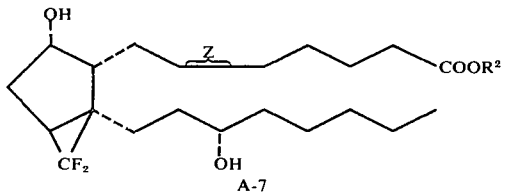
A-7

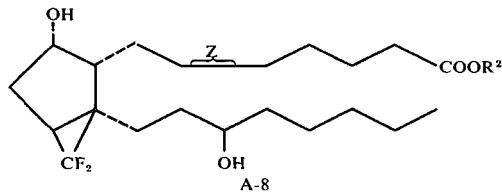
A-8

13. A racemic compound according to claim 9, formula A-1, wherein Z is a saturated linkage and $R^2$ is hydrogen, dl 9-keto-11α,12α-difluoromethylene-15α-hydroxyprostanoic acid.

14. A racemic compound according to claim 9, formula A-1, wherein Z is a cis double bond and $R^2$ is hydrogen, dl 9-keto-11α,12α-difluoromethylene-15α-hydroxyprost-5-cis-enoic acid.

15. A racemic compound according to claim 9, formula A-2, wherein Z is a cis double bond and $R^2$ is hydrogen, dl 9-keto-11α,12α-difluoromethylene-15β-hydroxyprost-5-cis-enoic acid.

16. A racemic compound according to claim 10, formula A-3, wherein Z is a saturated linkage and $R^2$ is hydrogen, dl 11α,12α-difluoromethylene-9α,15α-dihydroxyprostanoic acid.

17. A racemic compound according to claim 10, formula A-3, wherein Z is a saturated linkage and $R^2$ is methyl, dl 11α,12α-difluoromethylene-9α,15α-dihydroxyprostanoic acid methyl ester.

18. A racemic compound according to claim 10, formula A-3, wherein Z is a cis double bond and $R_2$ is hydrogen, dl 11α,12α-difluoromethylene-9α,15α-dihydroxyprost-5-cis-enoic acid.

19. A racemic compound according to claim 10, formula A-3, wherein Z is a cis double bond $R^2$ is methyl, dl 11α,12α-difluoromethylene-9α,15α-dihydroxyprost-5-cis-enoic acid methyl ester.

20. A racemic compound according to claim 10, formula A-4, wherein Z is a saturated linkage and $R^2$ is hydrogen, dl 11α,12α-difluoromethylene-9α,15β-dihydroxyprostanoic acid.

21. A racemic compound according to claim 10, formula A-4, wherein Z is a saturated linkage and $R^2$ is methyl, dl 11α,12α-difluoromethylene-9α,15β-dihydroxyprostanoic acid methyl ester.

22. A racemic compound according to claim 10, formula A-4, wherein Z is a cis double bond and $R^2$ is hydrogen, dl 11α,12α-difluoromethylene-9α,15β-dihydroxyprost-5-cis-enoic acid.

23. A racemic compound according to claim 10, formula A-4, wherein Z is a cis double bond and $R^2$ is methyl, dl 11α,12α-difluoromethylene-9α,15β-dihydroxyprost-5-cis-enoic acid methyl ester.

24. A compound according to claim 1, formula (B).

25. The compounds of claim 24 wherein R is keto and the side chain attached to the C-12 position is β, represented by the formula:

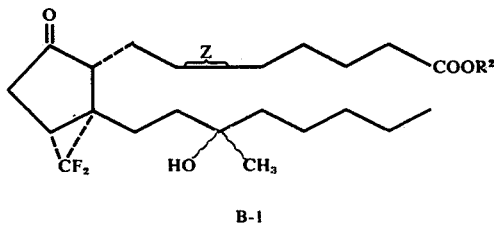

B-1

26. The compounds of claim 24 wherein R is α-hydroxy-β-hydrogen and the side chain attached to the C-12 position is β, represented by the formula:

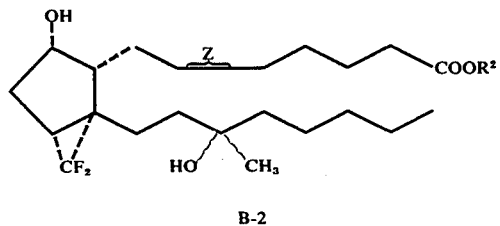

B-2

27. The compounds of claim 24 wherein R is keto and the side chain attached to the C-12 position is α, represented by the formula:

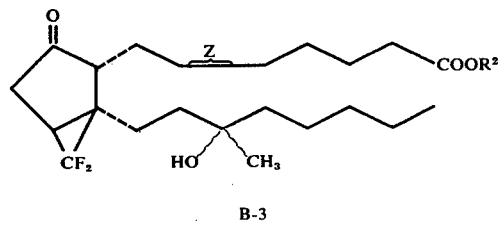

B-3

28. The compounds of claim 24 wherein R is α-hydroxy-β-hydrogen and the side chain attached to the C-12 position is α, represented by the formula:

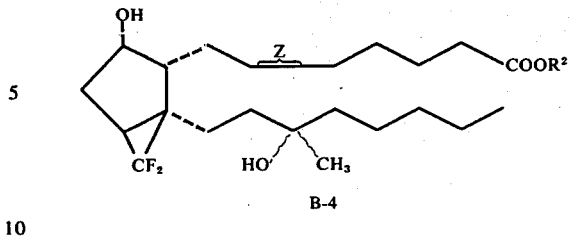

B-4

29. A racemic compound according to claim 25 wherein Z is a saturated linkage and $R^2$ is methyl, dl 9-keto-11α,12α-difluoromethylene-15 ⎰ -hydroxy-15 ⎰ -methylprostanoic acid methyl ester.

30. A racemic compound according to claim 25 wherein Z is a cis double bond and $R^2$ is methyl, dl 9-keto-11α,12α-difluoromethylene-15 ⎰ -hydroxy-15 ⎰ -methylprost-5-cis-enoic acid methyl ester.

31. A racemic compound according to claim 26 wherein Z is a saturated linkage and $R^2$ is hydrogen, dl 9α,15 ⎰ -dihydroxy-11α,12α-difluoromethylene-15 ⎰ -methylprostanoic acid.

32. A racemic compound according to claim 26 wherein Z is a saturated linkage and $R^2$ is methyl, dl 9α,15 ⎰ -dihydroxy-11α,12α-difluoromethylene-15 ⎰ -methylprostanoic acid methyl ester.

33. A racemic compound according to claim 26 wherein Z is a cis double bond and $R^2$ is hydrogen, dl 9α,15 ⎰ -dihydroxy-11α,12α-difluoromethylene-15 ⎰ -methylprost-5-cis-enoic acid.

34. A racemic compound according to claim 26, wherein Z is a cis-double bond and $R^2$ is methyl, dl 9α,15 ⎰ -dihydroxy-11α,12α-difluoromethylene-15 ⎰ -methylprost-5-cis-enoic acid methyl ester.

35. A racemic compound according to claim 27 wherein Z is a saturated linkage and $R^2$ is methyl, dl 9-keto-11β,12β-difluoromethylene-15 ⎰ -hydroxy-15 ⎰ -methyl-12α-prostanoic acid methyl ester.

36. A racemic compound according to claim 27, wherein Z is a cis double bond and $R^2$ is methyl, dl 9-keto-11β,12β-difluoromethylene-15 ⎰ -hydroxy-15 ⎰ -methyl-12α-prost-5-cis-enoic acid methyl ester.

37. A racemic compound according to claim 28 wherein Z is a saturated linkage and $R^2$ is methyl, dl 9α,15 ⎰ -dihydroxy-11β,12β-difluoromethylene-15⎰ -methyl-12α-prostanoic acid methyl ester.

38. A racemic compound according to claim 28 wherein Z is a cis double bond and $R^2$ is methyl, dl 9α,15 ⎰ -dihydroxy-11β,12β-difluoromethylene-15 ⎰ -methyl-12α-prost-5-cis-enoic acid methyl ester.

* * * * *